(12) United States Patent
Romero

(10) Patent No.: US 10,464,959 B2
(45) Date of Patent: Nov. 5, 2019

(54) INHERENTLY SELECTIVE PRECURSORS FOR DEPOSITION OF SECOND OR THIRD ROW TRANSITION METAL THIN FILMS

(71) Applicant: Intel Corporation, Santa Clara, CA (US)

(72) Inventor: Patricio E. Romero, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 48 days.

(21) Appl. No.: 15/570,989

(22) PCT Filed: Jun. 18, 2015

(86) PCT No.: PCT/US2015/036522
§ 371 (c)(1),
(2) Date: Oct. 31, 2017

(87) PCT Pub. No.: WO2016/204772
PCT Pub. Date: Dec. 22, 2016

(65) Prior Publication Data
US 2018/0222933 A1 Aug. 9, 2018

(51) Int. Cl.
*H01L 21/00* (2006.01)
*C07F 15/00* (2006.01)
(Continued)

(52) U.S. Cl.
CPC .......... *C07F 15/0053* (2013.01); *C07F 1/005* (2013.01); *C07F 1/02* (2013.01); *C07F 11/005* (2013.01); *C23C 16/04* (2013.01); *C23C 16/18* (2013.01); *H01L 21/28562* (2013.01); *H01L 21/28568* (2013.01); *H01L 21/7685* (2013.01); *H01L 21/76801* (2013.01);
(Continued)

(58) Field of Classification Search
CPC ........ C07F 15/0053; C07F 1/005; C07F 1/02; C07F 11/005; H01L 21/28562; H01L 21/28568; H01L 21/76801; H01L 21/7685; H01L 21/76876
See application file for complete search history.

(56) References Cited

U.S. PATENT DOCUMENTS

2005/0033075 A1   2/2005   Chi et al.
2008/0085365 A1   4/2008   Yamada et al.
(Continued)

FOREIGN PATENT DOCUMENTS

CN   1726303      1/2006
CN   101065349    10/2007
(Continued)

OTHER PUBLICATIONS

International Search Report for International Patent Application No. PCT/US2015/036522 dated Mar. 14, 2016, 13 pgs.
(Continued)

*Primary Examiner* — Richard A Booth
(74) *Attorney, Agent, or Firm* — Schwabe, Williamson & Wyatt, P.C.

(57) ABSTRACT

Inherently selective precursors for deposition of second or third row transition metal (e.g., tungsten or ruthenium) thin films are described. In an example, a ligand framework for second or third row transition metal complex formation includes a lithium complex.

19 Claims, 19 Drawing Sheets

(51) Int. Cl.
  *C07F 1/00*    (2006.01)
  *H01L 21/768*  (2006.01)
  *H01L 21/285*  (2006.01)
  *C23C 16/04*   (2006.01)
  *C23C 16/18*   (2006.01)
  *C07F 1/02*    (2006.01)
  *C07F 11/00*   (2006.01)

(52) U.S. Cl.
  CPC .. *H01L 21/76816* (2013.01); *H01L 21/76849* (2013.01); *H01L 21/76876* (2013.01); *H01L 21/76879* (2013.01); *H01L 21/76897* (2013.01)

(56) References Cited

U.S. PATENT DOCUMENTS

| | | |
|---|---|---|
| 2009/0035464 A1 | 2/2009 | Sato et al. |
| 2009/0199739 A1 | 8/2009 | Thompson et al. |
| 2009/0275164 A1 | 11/2009 | Chen |
| 2013/0273250 A1* | 10/2013 | Fujimura ............ C07C 211/65 427/255.394 |
| 2015/0105573 A1 | 4/2015 | Romero |

FOREIGN PATENT DOCUMENTS

| | | |
|---|---|---|
| CN | 101469005 | 7/2009 |
| EP | 1806352 | 7/2007 |

OTHER PUBLICATIONS

Pierre Braunstein et al., 'A quasi-covalent metal-metal bond in an early-late heterobimetallic Ti—Pt complex stabilized by phosphinoenolate ligands', Chem. Commun., 2003, pp. 610-611.

International Preliminary Report on Patentability for International Patent Application No. PCT/US2015/036522, dated Dec. 28, 2017, 9 pages.

Isamu Kinoshita et al., 'Preparation and resolution of the factris(2-amino-ethyldimethylphosphine)cobalt(III) complex and the absolute configuration of its(+)589-isomer determined by X-ray analysis', Chemistry Letters, 1980, vol. 9, pp. 95-98.

Search Report for European Patent Application No. 15895814.0, dated Jan. 18, 2019, 7 pgs.

Office Action from Chinese Patent Application No. 201580081010.5, dated Aug. 21, 2019, 9 pgs.

* cited by examiner

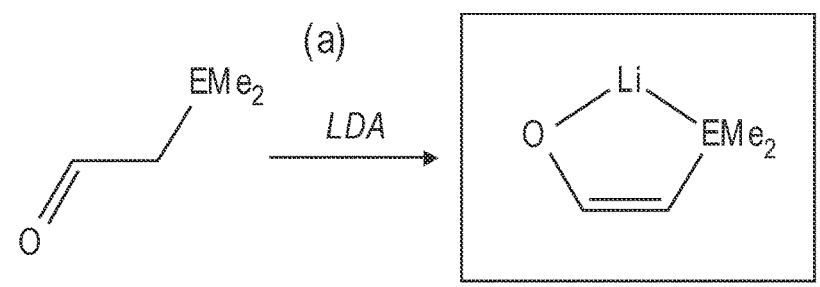
FIG. 3
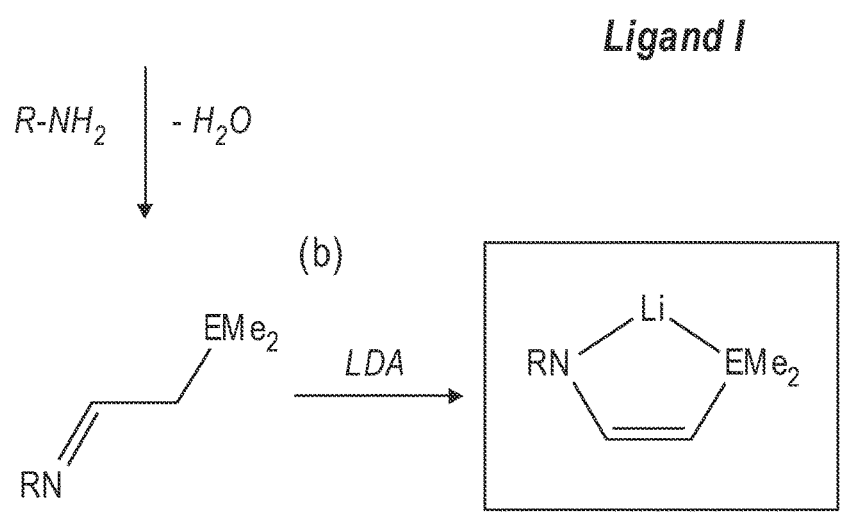
FIG. 4
R = Me, Et, $^i$Pr, $^t$Bu, sec-Bu, Me$_2$N
E = N, P
LDA = Lithium diisopropylamide
FIG. 2

(Only *mer* isomers shown)

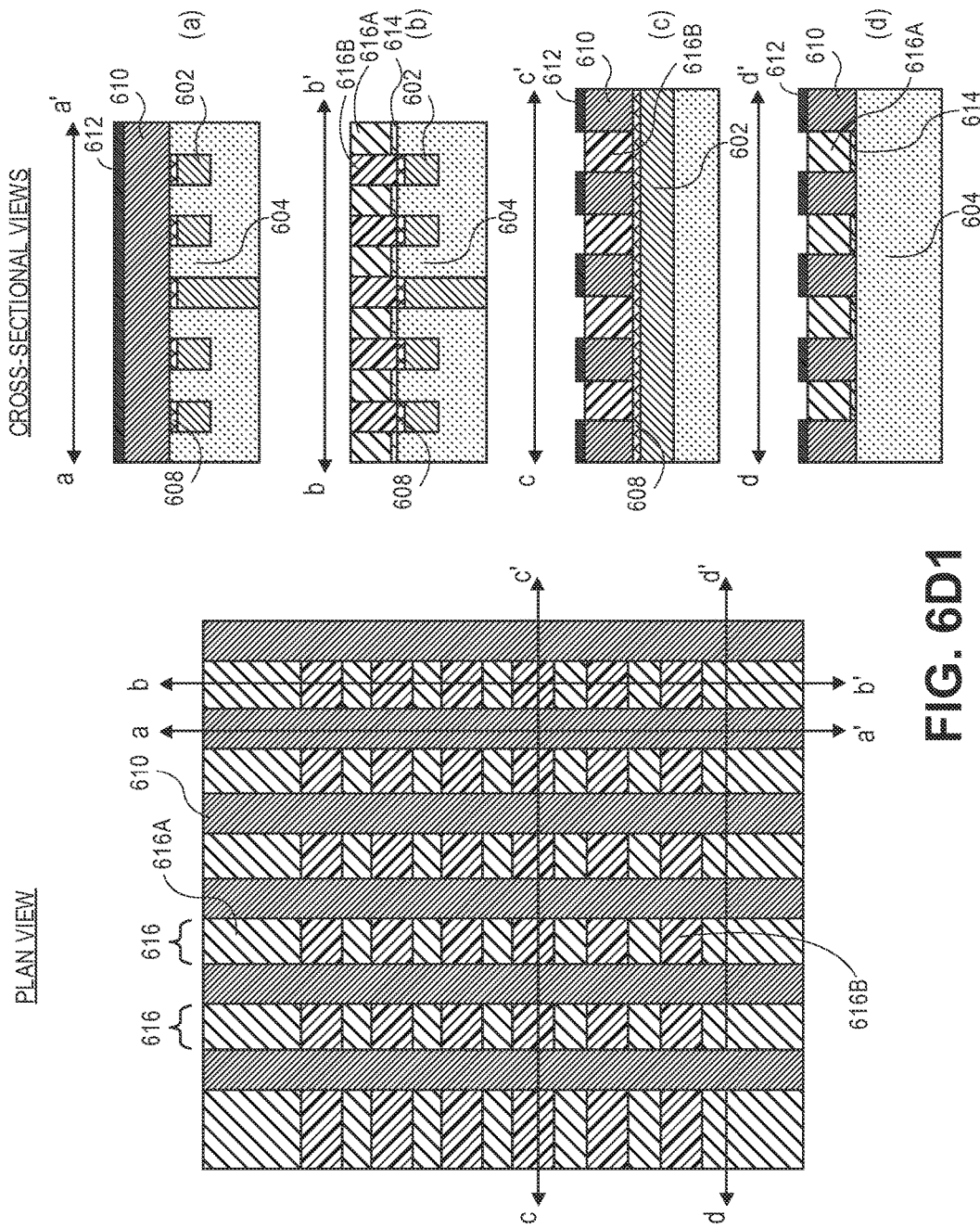

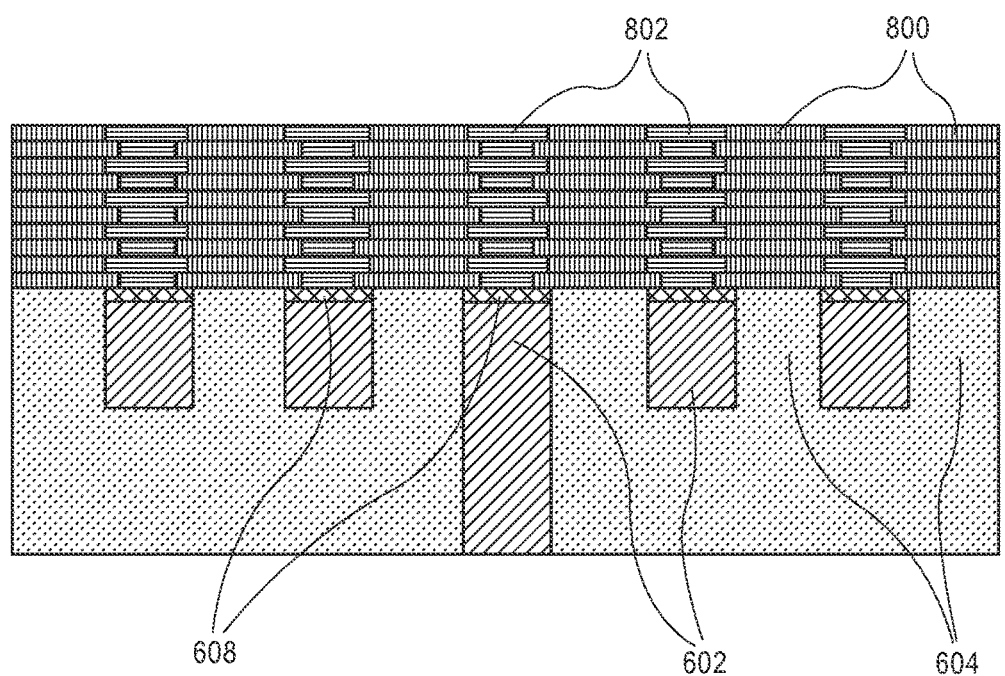
FIG. 6D2

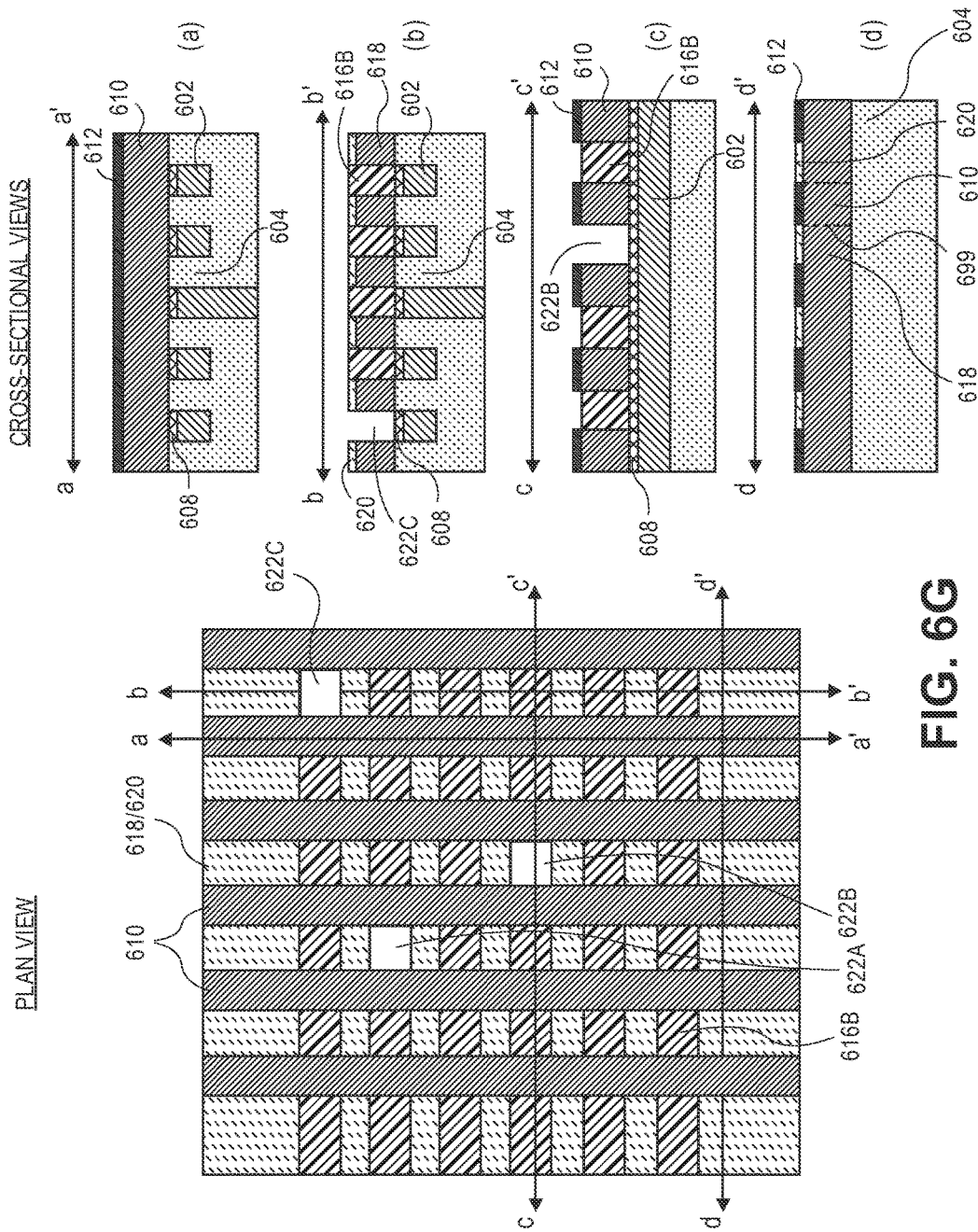

INHERENTLY SELECTIVE PRECURSORS FOR DEPOSITION OF SECOND OR THIRD ROW TRANSITION METAL THIN FILMS

CROSS-REFERENCE TO RELATED APPLICATION

This patent application is a U.S. National Phase Application under 35 U.S.C. § 371 of International Application No. PCT/US2015/036522, filed Jun. 18, 2015, entitled "INHERENTLY SELECTIVE PRECURSORS FOR DEPOSITION OF SECOND OR THIRD ROW TRANSITION METAL THIN FILMS," which designates the United States of America, the entire disclosure of which is hereby incorporated by reference in its entirety and for all purposes.

TECHNICAL FIELD

Embodiments of the invention are in the field of semiconductor structures and processing and, in particular, inherently selective precursors for deposition of second or third row transition metal thin films.

BACKGROUND

For the past several decades, the scaling of features in integrated circuits has been a driving force behind an ever-growing semiconductor industry. Scaling to smaller and smaller features enables increased densities of functional units on the limited real estate of semiconductor chips.

In a first aspect, integrated circuits commonly include electrically conductive microelectronic structures, which are known in the arts as vias, to electrically connect metal lines or other interconnects above the vias to metal lines or other interconnects below the vias. Vias are typically formed by a lithographic process. Representatively, a photoresist layer may be spin coated over a dielectric layer, the photoresist layer may be exposed to patterned actinic radiation through a patterned mask, and then the exposed layer may be developed in order to form an opening in the photoresist layer. Next, an opening for the via may be etched in the dielectric layer by using the opening in the photoresist layer as an etch mask. This opening is referred to as a via opening. Finally, the via opening may be filled with one or more metals or other conductive materials to form the via.

In the past, the sizes and the spacing of vias has progressively decreased, and it is expected that in the future the sizes and the spacing of the vias will continue to progressively decrease, for at least some types of integrated circuits (e.g., advanced microprocessors, chipset components, graphics chips, etc.). One measure of the size of the vias is the critical dimension of the via opening. One measure of the spacing of the vias is the via pitch. Via pitch represents the center-to-center distance between the closest adjacent vias. When patterning extremely small vias with extremely small pitches by such lithographic processes, several challenges present themselves, especially when the pitches are around 70 nanometers (nm) or less and/or when the critical dimensions of the via openings are around 35 nm or less.

One such challenge is that the overlay between the vias and the overlying interconnects, and the overlay between the vias and the underlying landing interconnects, generally need to be controlled to high tolerances on the order of a quarter of the via pitch. As via pitches scale ever smaller over time, the overlay tolerances tend to scale with them at an even greater rate than lithographic equipment is able to keep up. Another such challenge is that the critical dimensions of the via openings generally tend to scale faster than the resolution capabilities of the lithographic scanners. Shrink technologies exist to shrink the critical dimensions of the via openings. However, the shrink amount tends to be limited by the minimum via pitch, as well as by the ability of the shrink process to be sufficiently optical proximity correction (OPC) neutral, and to not significantly compromise line width roughness (LWR) and/or critical dimension uniformity (CDU). Yet another such challenge is that the LWR and/or CDU characteristics of photoresists generally need to improve as the critical dimensions of the via openings decrease in order to maintain the same overall fraction of the critical dimension budget. However, currently the LWR and/or CDU characteristics of most photoresists are not improving as rapidly as the critical dimensions of the via openings are decreasing. A further such challenge is that the extremely small via pitches generally tend to be below the resolution capabilities of even extreme ultraviolet (EUV) lithographic scanners. As a result, commonly two, three, or more different lithographic masks may be used, which tend to increase the costs. At some point, if pitches continue to decrease, it may not be possible, even with multiple masks, to print via openings for these extremely small pitches using EUV scanners.

Thus, improvements are needed in the area of via manufacturing technologies.

In a second aspect, multi-gate transistors, such as tri-gate transistors, have become more prevalent as device dimensions continue to scale down. In conventional processes, tri-gate or other non-planar transistors are generally fabricated on either bulk silicon substrates or silicon-on-insulator substrates. In some instances, bulk silicon substrates are preferred due to their lower cost and compatibility with the existing high-yielding bulk silicon substrate infrastructure. Scaling multi-gate transistors has not been without consequence, however. As the dimensions of these fundamental building blocks of microelectronic circuitry are reduced and as the sheer number of fundamental building blocks fabricated in a given region is increased, the constraints on the semiconductor processes used to fabricate these building blocks have become overwhelming.

Thus, improvements are needed in the area of non-planar transistor manufacturing technologies.

BRIEF DESCRIPTION OF THE DRAWINGS

FIG. 2 is a schematic showing formation of a first class (Ligand I) and a second class (Ligand II) of ligand frameworks for second and third row transition metal complex formation, in accordance with an embodiment of the present invention.

FIG. 3 illustrates the first class (Ligand I) of ligand frameworks for second and third row transition metal complex formation, in accordance with an embodiment of the present invention.

FIG. 4 illustrates the second class (Ligand II) of ligand frameworks for second and third row transition metal complex formation, in accordance with an embodiment of the present invention.

FIGS. 6A-6L illustrate portions of integrated circuit layers representing various operations in a method of self-aligned via and metal patterning, in accordance with an embodiment of the present invention, where:

FIG. 6A illustrates a plan view and corresponding cross-sectional views of options for a previous layer metallization structure;

FIG. 6B illustrates a plan view and corresponding cross-sectional views of the structure of FIG. 6A following formation of interlayer dielectric (ILD) lines above the structure of FIG. 6A;

FIG. 6C illustrates a plan view and corresponding cross-sectional views of the structure of FIG. 6B following selective differentiation of all the potential via locations from all of the plug locations;

FIG. 6D1 illustrates a plan view and corresponding cross-sectional views of the structure of FIG. 6C following differential polymer addition to the exposed portions of underlying metal and ILD lines of FIG. 6C;

FIG. 6D2 illustrates a cross-sectional view of the structure of FIG. 6B following selective material deposition on the exposed portions of underlying metal and ILD lines, in accordance with another embodiment of the present invention;

FIG. 6E illustrates a plan view and corresponding cross-sectional views of the structure of FIG. 6D1 following removal of one species of polymer;

FIG. 6F illustrates a plan view and corresponding cross-sectional views of the structure of FIG. 6E following formation of an ILD material in the locations opened upon removal of the one species of polymer;

FIG. 6G illustrates a plan view and corresponding cross-sectional views of the structure of FIG. 6F following via patterning;

FIG. 6H illustrates a plan view and corresponding cross-sectional views of the structure of FIG. 6G following via formation using a selective metal deposition process;

FIG. 6I illustrates a plan view and corresponding cross-sectional views of the structure of FIG. 6H following removal of the second species of polymer and replacement with an ILD material;

FIG. 6J illustrates a plan view and corresponding cross-sectional views of the structure of FIG. 6I following patterning of a resist or mask in selected plug locations;

FIG. 6K illustrates a plan view and corresponding cross-sectional views of the structure of FIG. 6J following hardmask removal and ILD layer recessing;

FIG. 6L illustrates a plan view and corresponding cross-sectional views of the structure of FIG. 6K following metal line formation.

DESCRIPTION OF THE EMBODIMENTS

Figure 1:
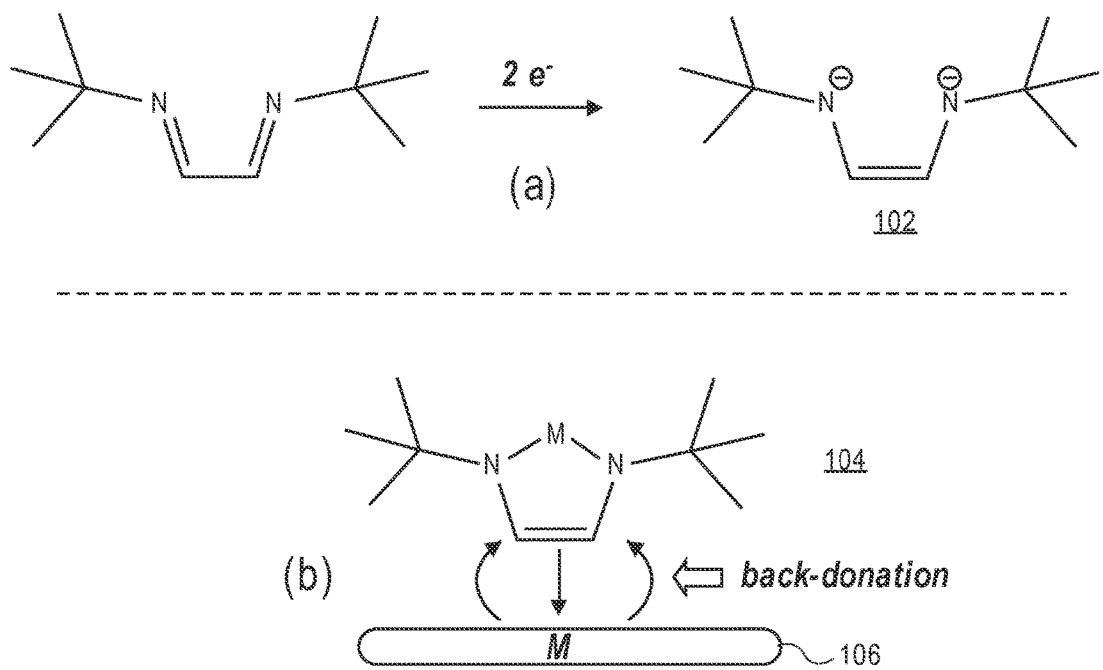
FIG. 1 is a schematic showing state of the art selective CVD deposition of a metal such as Fe, Co, Ni, Cr and Mn by using diazabutadiene ligands as stabilizing scaffolds.

Inherently selective precursors for deposition of second or third row transition metal (e.g., tungsten or ruthenium) thin films are described. In the following description, numerous specific details are set forth, such as specific integration and material regimes, in order to provide a thorough understanding of embodiments of the present invention. It will be apparent to one skilled in the art that embodiments of the present invention may be practiced without these specific details. In other instances, well-known features, such as integrated circuit design layouts, are not described in detail in order to not unnecessarily obscure embodiments of the present invention. Furthermore, it is to be understood that the various embodiments shown in the Figures are illustrative representations and are not necessarily drawn to scale.

One or more embodiments described herein are directed to precursor and process design for metal atomic layer deposition (ALD) or chemical vapor deposition (CVD). Aspects may include the fabrication of conformal thin metal films, and thin metal film synthesis for device, interconnect and system-on-chip (SOC) applications. In an exemplary embodiment described in greater detail below, a second or third row transition metal (e.g., tungsten or ruthenium) film is selectively deposited on a metal surface (e.g., copper or cobalt) and a directed self-assembly (DSA) processing scheme is subsequently performed on the tungsten or ruthenium surface.

To provide context, the ability to selectively deposit metal on one surface over another can enable new integration and patterning schemes as well as decrease the number of manufacturing operations. One or more embodiments described herein involve the use of a precursor class with built-in structural features that enable the ALD or CVD of transition metals on metallic surfaces. The ALD or CVD is effected while avoiding deposition on adjacent dielectric surfaces such as $SiO_2$ or low-k interlayer dielectrics (ILDs). The selectivity is inherent to the precursor and, as such, chemical passivation of the undesired surface may not be needed. In an embodiment, molecules described herein allow for the deposition of metals with direct impact on the ability to enable direct self-assembly (DSA) of polymeric units.

One or more embodiments described herein provide an approach for selectively depositing metallic films by a thermal ALD or CVD, while avoiding undesirable metallic contamination of neighboring (e.g., low-k) dielectric layers. Depending on substrate, approaches described herein provide a direct method for depositing "metal on metal" with or without the need for pre-treatment of either the metallic or neighboring dielectric surface.

In addition to the significant benefits of the selective deposition approaches described herein, other advantages for manufacturing may be realized such as the circumvention of substrate passivation or the use of lithographic patterning to direct the selectivity. The approaches described herein may be applicable to a variety of different metals and can be employed in self-aligned next layer interconnect schemes, as described in greater detail below. Furthermore, the metals that are central to embodiments of the present invention (e.g., Ru, W) are significant enablers as substrate materials for DSA patterning schemes.

More specifically, embodiments described herein involve approaches for the deposition of a variety of transition metal films selectively on metal surfaces, while avoiding deposition on contiguous low-k dielectric substrates. The deposition is accomplished by thermal ALD or CVD using a volatile metal precursor, with a specific ligand make-up and may or may not use a suitable co-reactant. The selective deposition is accomplished with or without pretreatment of the low-k substrate. The nature of the process (e.g., precursor type, surfaces and deposition schemes) renders the approaches directly applicable on DSA integration and self-aligned patterning schemes.

As eluded to above, there is currently no unified solution for selective deposition of metals on metals in semiconductor processing. However, embodiments of the present invention provide several general benefits from a manufacturing point of view. First, films are deposited by thermal ALD or CVD in order to maximize film conformality and minimize damage to device structures as can otherwise be observed with plasma-enhanced processes. Second, the precursor design is applicable to a variety of metals including but not limited to tungsten (W) and ruthenium (Ru) under thermal deposition conditions. Third, in some cases, the selective deposition process is achieved without any special pretreatment of the exposed, competing surfaces (e.g., without chemical passivation of either the low-k dielectric or pre-cleaning of the metal surface). Fourth, the process does not require the use of lithographic patterning schemes or masks to define the selectivity of the process. Instead, the process relies on inherent differences in chemical reactivity. Fifth, selective metal on metal growth can be used to enable the patterning by DSA due to the selective affinity of the polymeric brush units for metals such as W and Ru.

It is to be recognized that the selective CVD deposition of Fe, Co, Ni, Cr and Mn metal by using diazabutadiene ligands as stabilizing scaffolds has been previously described. In the large majority of cases, such deposition is achieved without the need for any special pretreatment. As such, the nature of the selectivity is embedded in the precursor itself. Density Functional Theory (DFT) calculations revealed that the selectivity in such cases is directed by the ligand framework, specifically through the olefinic C—C bond positioned in the chelating portion of the diazabutadiene ligand. This bond has a high affinity for metal substrates, since a synergic arrangement favors a strong bond between the electron-rich alkene and the surface, through a regular σ-donating bond and an additional it-back donation from the metal surface itself.

FIG. 1 is a schematic showing state of the art selective CVD deposition of a metal such as Fe, Co, Ni, Cr and Mn by using diazabutadiene ligands as stabilizing scaffolds. Referring to FIG. 1, scheme (a) shows formation of diazabutadiene ligand 102 having a negative charge associated with each nitrogen atom. One or more diazabutadiene ligands 102 can be used to form a metal complex 104 where the diazabutadiene ligand 102 chelates the metal M (e.g., M=Fe, Co, Ni, Cr or Mn) in a bidentate fashion. As shown in scheme (b), the metal complex 104 can be used to deposit a metal (M) layer 106 via a back-donation mechanism, as is depicted in FIG. 1.

With reference again to FIG. 1, due to bonding differences between first and second/third row metals, the same ligand motif (i.e., diazabutadiene (DABD)) cannot be directly translated or extended in a straightforward manner to second and third row metals. In cases where homoleptic motifs of the form $M(DABD)_x$ (e.g., with x generally 3 and M=Ru or W) could be accessed, the species showed both significantly lower thermal stability and volatility, compared to first-row counterparts. Although not to be bound by theory, such degradation in thermal stability and volatility may be due in part to the higher molecular weights implicated in such complexes. By contrast, in accordance with one or more embodiments described herein, good thermal stability and volatility properties are extended to second and third-row transition metals, primarily Ru and W, using inherent selectivity based on new ligands designed to overcome the limitations described above with respect to diazabutadiene based complexes.

FIG. 2 is a schematic showing formation of a first class (Ligand I) and a second class (Ligand II) of ligand frameworks for second and third row transition metal complex formation, in accordance with an embodiment of the present invention. FIG. 3 illustrates the first class (Ligand I) of ligand frameworks for second and third row transition metal complex formation. FIG. 4 illustrates the second class (Ligand II) of ligand frameworks for second and third row transition metal complex formation.

Referring to scheme (a) of FIG. 2 and to corresponding Ligand I of FIG. 3, lithium diisopropylamide (LDA) treatment is used to generate a lithium complex of Ligand I, where E is N or P. Referring to scheme (b) of FIG. 2 and to corresponding Ligand II of FIG. 4, primary amine treatment/condensation followed by lithium diisopropylamide (LDA) treatment is used to generate a lithium complex of Ligand II, where E is N or P, and where R is methyl (Me), ethyl (Et), iso-propyl ($^i$Pr), tert-butyl ($^t$Bu), sec-butyl (sec-Bu), or dimethyl amino ($Mc_2N$). It is to be appreciated that the methyl groups associated with E may be larger than methyl, but may still be relatively small for volatility considerations. For example, in another embodiment, in place of $EMe_2$, the diethyl moiety ($EET_2$) may be used.

With reference again to FIGS. 2, 3 and 4, the ligand designs described can be implemented to achieve selectivity for second and third row transition metals along the same lines as described above for diazabutadiene systems for first row transition metals. Specifically, in an embodiment, the presence of an olefinic functionality is used to increase affinity for a metal substrate. In an embodiment, the olefin bond, however, is formed by selective deprotonation in order to lock the alkene in a cis conformation. Unlike diazabutadienes, Ligand I and Ligand II frameworks allow straightforward incorporation of small (e.g., Me, Et) R substituents in the coordinating heteroatoms. Such a condition may be necessary for high volatility. The anionic salts shown in FIGS. 3 and 4 serve as starting materials for the synthesis of homo- and heteroleptic complexes of second and third row transition metals, such as W or Ru.

Figure 5:
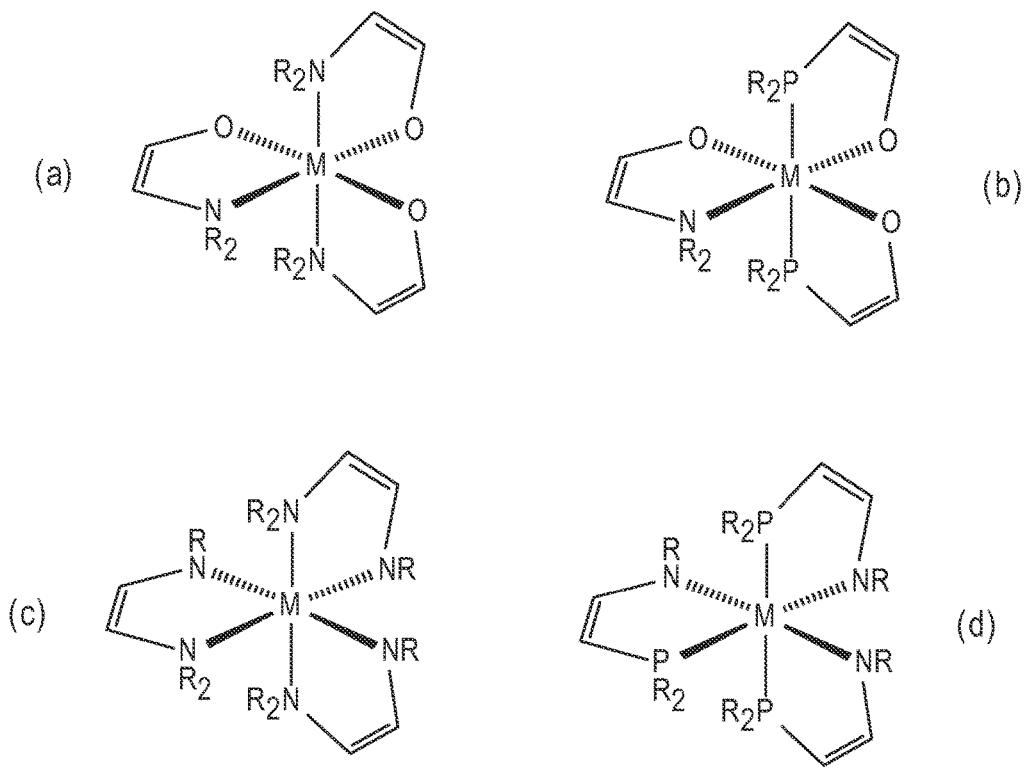
FIG. 5 illustrates examples of second and third row transition metal complexes derived from the ligands of FIGS. 3 and 4, in accordance with an embodiment of the present invention.

FIG. 5 illustrates examples of second and third row transition metal complexes derived from the ligands of FIGS. 3 and 4, in accordance with an embodiment of the present invention. Referring to FIG. 5, the metal complex (a) is an exemplary complex having three ligands of ligand type Ligand I, where E is N. The metal complex (b) is an exemplary complex having three ligands of ligand type Ligand I, where E is P. The metal complex (c) is an exemplary complex having three ligands of ligand type Ligand II, where E is N. The metal complex (d) is an exemplary complex having three ligands of ligand type Ligand II, where E is P. For all complexes (a)-(d), in an embodiment, $R_2$ is $Mc_2$ or $Et_2$, R is an organic group such as, but not limited to, methyl (Me), ethyl (Et), iso-propyl ($^i$Pr), tert-butyl ($^t$Bu), sec-butyl (sec-Bu), or dimethyl amino ($Mc_2N$), and M is a second or third row transition metal such as, but not limited to, tungsten (W) or ruthenium (Ru). It is to be appreciated that only mer isomers are depicted in FIG. 5. Embodiments described herein also contemplate isomers of the structures (a)-(d).

With reference again to FIG. 5, in an embodiment, a complex such as one of the complexes (a)-(d) or their isomers is used in an atomic layer deposition or a chemical vapor deposition processing scheme to deposit a second or third row transition metal layer. In one such embodiment, a complex such as one of the complexes (a)-(d) or their isomers is used to deposit a high purity tungsten layer by ALD or CVD. In another embodiment, a complex such as one of the complexes (a)-(d) or their isomers is used to deposit a high purity ruthenium layer by ALD or CVD. Such ALD or CVD processes may be used to in a selective deposition scheme. For example, in one embodiment, an integration scheme based on directed self-assembly (DSA) for interconnect fabrication includes deposition using a complex such as one of the complexes (a)-(d) or their isomers. It is to be appreciated that the presence of nitrogen, carbon or phosphorus as minor impurities in the deposited films may be an indication of the use of such complexes in ALD or CVD processing.

Thus, embodiments are directed to forming ultrathin, conformal metallic films using inherently selective ALD/CVD processing. Although not so limited, embodiments may be implemented to fabricate thin metal films of high purity having a thickness approximately equal to or less than 10 nanometers, at relatively low temperatures. Co-reactants, if used in the deposition process, could range from $H_2$ to $NH_3$, TMA, hydrazine, hydrosilanes, boranes, $O_2$, $O_3$, $H_2O$ etc.

In an embodiment, then, a method of fabricating a thin metal film includes introducing precursor molecules proximate to a metal surface on or above a substrate. Each of the precursor molecules includes a second or third row transition metal center complexed with three heteroleptic bidentate ligands. The method also includes depositing a second or third row transition metal layer on the metal surface by thermally dissociating the ligands from the precursor molecules. In one embodiment, thermally dissociating the ligands from the precursor molecules involves heating to a temperature approximately in the range of 50-600 degrees Celsius. In one embodiment, depositing the second or third row transition metal layer on the metal surface involves depositing selectively on the metal surface without depositing on an adjacent dielectric surface. In one embodiment, depositing the second or third row transition metal layer on the metal surface involves forming the second or third row transition metal layer to a thickness approximately equal to or less than 10 nanometers. In one embodiment, depositing the second or third row transition metal layer comprises using an atomic layer deposition (ALD) or a chemical vapor deposition (CVD) process. In one embodiment, depositing the second or third row transition metal layer involves depositing a tungsten or ruthenium layer.

One or more embodiments described herein are directed to selective area deposition of metal films by atomic layer deposition (ALD) and/or chemical vapor deposition (CVD). To provide context, the ability to selectively deposit metal on one surface over another can enable new integration and patterning schemes as well as decrease the number of manufacturing operations otherwise associated with a semiconductor manufacturing process. In accordance with an embodiment of the present invention, as described above, a precursor class is described with built-in structural features that enable the ALD or CVD of a second or third row transition metal (e.g., tungsten or ruthenium) on metallic surfaces while avoiding deposition on adjacent dielectric surfaces such as silicon dioxide ($SiO_2$) or low-k inter layer dielectric layers (ILDs).

In a first particular embodiment, a metallization layer surface is prepared for enhanced direct self-assembly (DSA) using an ALD or CVD process described above. In one particular embodiment, metals capping layers are formed to direct self-assembly of a brush process, examples of which are described in greater detail below. In a second particular embodiment, the approaches described herein can be used to enable electroless via bottom-up fill and can also enable self-aligned bottom-up interconnect design, examples of which are described in greater detail below. As such, one or more embodiments provide approaches for selectively depositing second or third row transition metal (e.g., tungsten or ruthenium) films by an ALD or CVD process, while avoiding undesirable metallic contamination of neighboring (low-k) dielectric layers. Such processes can be employed in self-aligned next layer interconnect patterning scheme, an example of which is described below.

Thus, one or more embodiments described herein are directed to self-aligned via and plug patterning. The self-aligned aspect of the processes described herein may be based on a directed self-assembly (DSA) mechanism, as described in greater detail below. However, it is to be understood that selective growth mechanisms may be employed in place of, or in combination with, DSA-based approaches. In an embodiment, processes described herein enable realization of self-aligned metallization using selective metal deposition for back-end of line feature fabrication.

To provide context, patterning and aligning of features at less than approximately 50 nanometer pitch requires many reticles and critical alignment strategies that are extremely expensive for a semiconductor manufacturing process. Generally, embodiments described herein involve the fabrication of metal and via patterns based on the positions of an underlying layer. That is, in contrast to conventional top-down patterning approaches, a metal interconnect process is effectively reversed and built from the previous layer up. This is in contrast to a conventional approach where an interlayer dielectric (ILD) is first deposited, with a pattern for metal and via layers subsequently patterned therein. In the conventional approach, alignment to a previous layer is performed using a lithography scanner alignment system. The ILD is then etched.

More specifically, one or more embodiments are directed to an approach that employs an underlying metal as a template to build the conductive vias and non-conductive spaces or interruptions between metals (referred to as "plugs"). Vias, by definition, are used to land on a previous layer metal pattern. In this vein, embodiments described herein enable a more robust interconnect fabrication scheme since alignment by lithography equipment is no longer relied on. Such an interconnect fabrication scheme can be used to save numerous alignment/exposures, can be used to improve electrical contact (e.g., by reducing via resistance), and can be used to reduce total process operations and processing time otherwise required for patterning such features using conventional approaches.

As illustrated below, self-aligned via and metal patterning approaches described herein may include one or more of the following aspects or attributes: (a) a bottom up super-self-aligned via/metal patterning process is enabled; (b) a previous layer metal is used to direct positions of vias on the layer formed above; (c) a process that generates every possible via and metal line end position but maintains only required or desired via and metal line end positions; (d) the position and shape of vias and metal line ends are pre-formed from a previous layer pattern; (e) an intersection of metal below and above naturally forms the fully self-aligned via positions; (f) via and plugs position, size and shape are defined by a pre-existing grating lithography from underlying metal layers; (g) via and plug lithography is required only for selecting one or another and does not affect the position, shape or size of the features (e.g., LWR is irrelevant); (h) processes described herein may be characterized as an upside down dual-damascene or via/plug first approach; (i) corresponding lithography photoresist design can be simplified since greater tolerance is achieved in the selection of via and plug locations within a layer (this may be referred to as a "bucket" approach, where a photoresist is merely used to fill a plurality of generated holes, where only certain holes are subsequently selected to be maintained or deleted); (j) LWR is not critical and faster resists can be used; (k) the size of the features can be fabricated as a single shape and size, and may be applicable for electron beam direct write (EBDW) processes; and (k) via design rules are simplified and all possible vias are allowed in any geometric configuration, where the size of the vias is completely defined by the intersection of the metal above and below.

FIGS. 6A-6L illustrate portions of integrated circuit layers representing various operations in a method of self-aligned via and metal patterning, in accordance with an embodiment of the present invention. In each illustration at each described operation, plan views are shown on the left-hand side, and corresponding cross-sectional views are shown on the right-hand side. These views will be referred to herein as corresponding cross-sectional views and plan views.

Figure 6A:
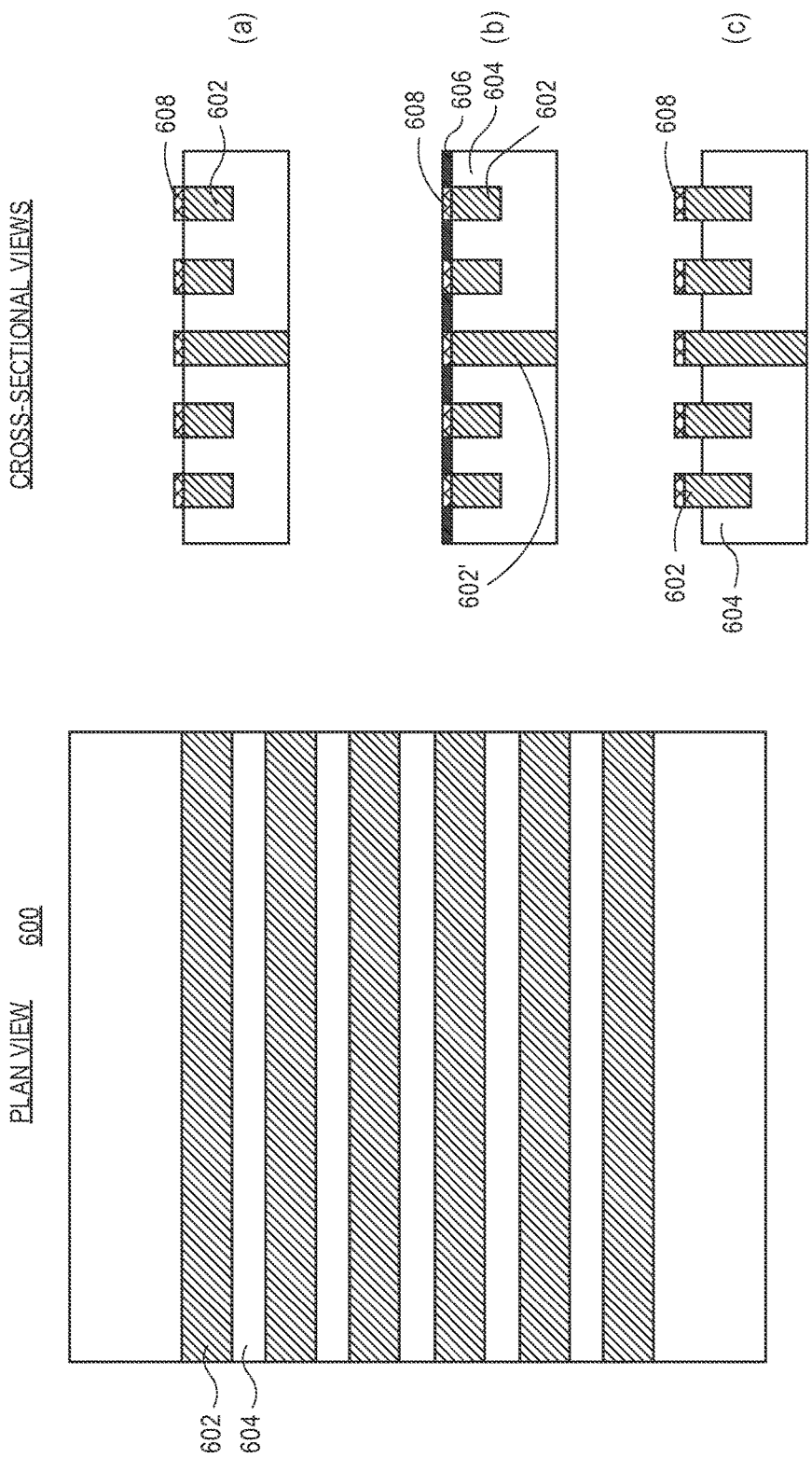

FIG. 6A illustrates a plan view and corresponding cross-sectional views of options for a previous layer metallization structure, in accordance with an embodiment of the present invention. Referring to the plan view and corresponding cross-section view option (a), a starting structure 600 includes a pattern of metal lines 602 and interlayer dielectric (ILD) lines 604. The starting structure 600 may be patterned in a grating-like pattern with metal lines spaced at a constant pitch and having a constant width (e.g., for a DSA embodiment, but not necessarily needed for a directed selective growth embodiment), as is depicted in FIG. 6A. The pattern, for example, may be fabricated by a pitch halving or pitch quartering approach. Some of the lines may be associated with underlying vias, such as line 602' shown as an example in the cross-sectional views.

Referring again to cross-section (a), a second or third row transition metal capping layer 608 is formed on the metal lines 602. In an embodiment, the second or third row transition metal capping layer 608 is formed using an inherently selective deposition process selective to the ILD lines 604. In one such embodiment, a complex such as one of the complexes (a)-(d) of FIG. 5 or their isomers is used in an atomic layer deposition or a chemical vapor deposition processing scheme to deposit a second or third row transition metal layer. In one such embodiment, a complex such as one of the complexes (a)-(d) or their isomers is used to deposit a high purity tungsten layer by ALD or CVD. In another embodiment, a complex such as one of the complexes (a)-(d) or their isomers is used to deposit a high purity ruthenium layer by ALD or CVD. In an embodiment, the second or third row transition metal capping layer 608 is used to enable a selective growth and/or self-assembly described below in association with subsequent processing operations.

Referring again to FIG. 6A, alternative option (b) addresses a situation where an additional film 606 is formed (e.g., deposited, grown, or left as an artifact remaining from a previous patterning process) on a surface of the interlayer dielectric lines 604. Furthermore, although the metal lines 602 and the interlayer dielectric lines 604 are depicted as co-planar in cross-section (a), in other embodiments, they are not co-planar. For example, in cross-section (c), the metal lines 602 protrude above the interlayer dielectric lines 604.

Referring again to example cross-section (b), the additional layer 606 can be used as a hardmask (HM) or protection layer or be used to enable a selective growth and/or self-assembly described below in association with subsequent processing operations. Such an additional layer 606 may also be used to protect the ILD lines from further processing. Referring again to example (c), it may also be possible to recess the ILD lines with a protective hardmask material on the surface of 604. Overall, there exist numerous options at this stage for preparing ultimately underlying surfaces for a selective or directed self-assembly process.

In an embodiment, as used throughout the present description, interlayer dielectric (ILD) material, such as the material of the interlayer dielectric lines 604, is composed of or includes a layer of a dielectric or insulating material. Examples of suitable dielectric materials include, but are not limited to, oxides of silicon (e.g., silicon dioxide ($SiO_2$)), doped oxides of silicon, fluorinated oxides of silicon, carbon doped oxides of silicon, various low-k dielectric materials known in the arts, and combinations thereof. The interlayer dielectric material may be formed by conventional techniques, such as, for example, chemical vapor deposition (CVD), physical vapor deposition (PVD), or by other deposition methods.

In an embodiment, as is also used throughout the present description, interconnect material, such as the material of metal lines 602, is composed of one or more metal or other conductive structures. A common example is the use of copper lines and structures that may or may not include barrier layers between the copper and surrounding ILD material. As used herein, the term metal includes alloys, stacks, and other combinations of multiple metals. For example, the metal interconnect lines may include barrier layers, stacks of different metals or alloys, etc. The interconnect lines are also sometimes referred to in the arts as traces, wires, lines, metal, or simply interconnect. As will be described further below, top surfaces of the lower interconnect lines may be used for self-aligned via and plug formation.

In an embodiment, as is also used throughout the present description, hardmask materials, such, as layer 606 if included as a hardmask, are composed of dielectric materials different from the interlayer dielectric material. In one embodiment, different hardmask materials may be used in different regions so as to provide different growth or etch selectivity to each other and to the underlying dielectric and metal layers. In some embodiments, a hardmask layer includes a layer of a nitride of silicon (e.g., silicon nitride) or a layer of an oxide of silicon, or both, or a combination thereof. Other suitable materials may include carbon-based materials. In another embodiment, a hardmask material includes a metal species. For example, a hardmask or other overlying material may include a layer of a nitride of titanium or another metal (e.g., titanium nitride). Potentially lesser amounts of other materials, such as oxygen, may be included in one or more of these layers. Alternatively, other hardmask layers known in the arts may be used depending upon the particular implementation. The hardmask layers maybe formed by CVD, PVD, or by other deposition methods.

It is to be understood that the layers and materials described in association with FIG. 6A are typically formed on or above an underlying semiconductor substrate or structure, such as underlying device layer(s) of an integrated circuit. In an embodiment, an underlying semiconductor substrate represents a general workpiece object used to manufacture integrated circuits. The semiconductor substrate often includes a wafer or other piece of silicon or another semiconductor material. Suitable semiconductor substrates include, but are not limited to, single crystal silicon, polycrystalline silicon and silicon on insulator (SOI), as well as similar substrates formed of other semiconductor materials. The semiconductor substrate, depending on the stage of manufacture, often includes transistors, integrated circuitry, and the like. The substrate may also include semiconductor materials, metals, dielectrics, dopants, and other materials commonly found in semiconductor substrates. Furthermore, the structure depicted in FIG. 6A may be fabricated on underlying lower level interconnect layers.

Figure 6B:
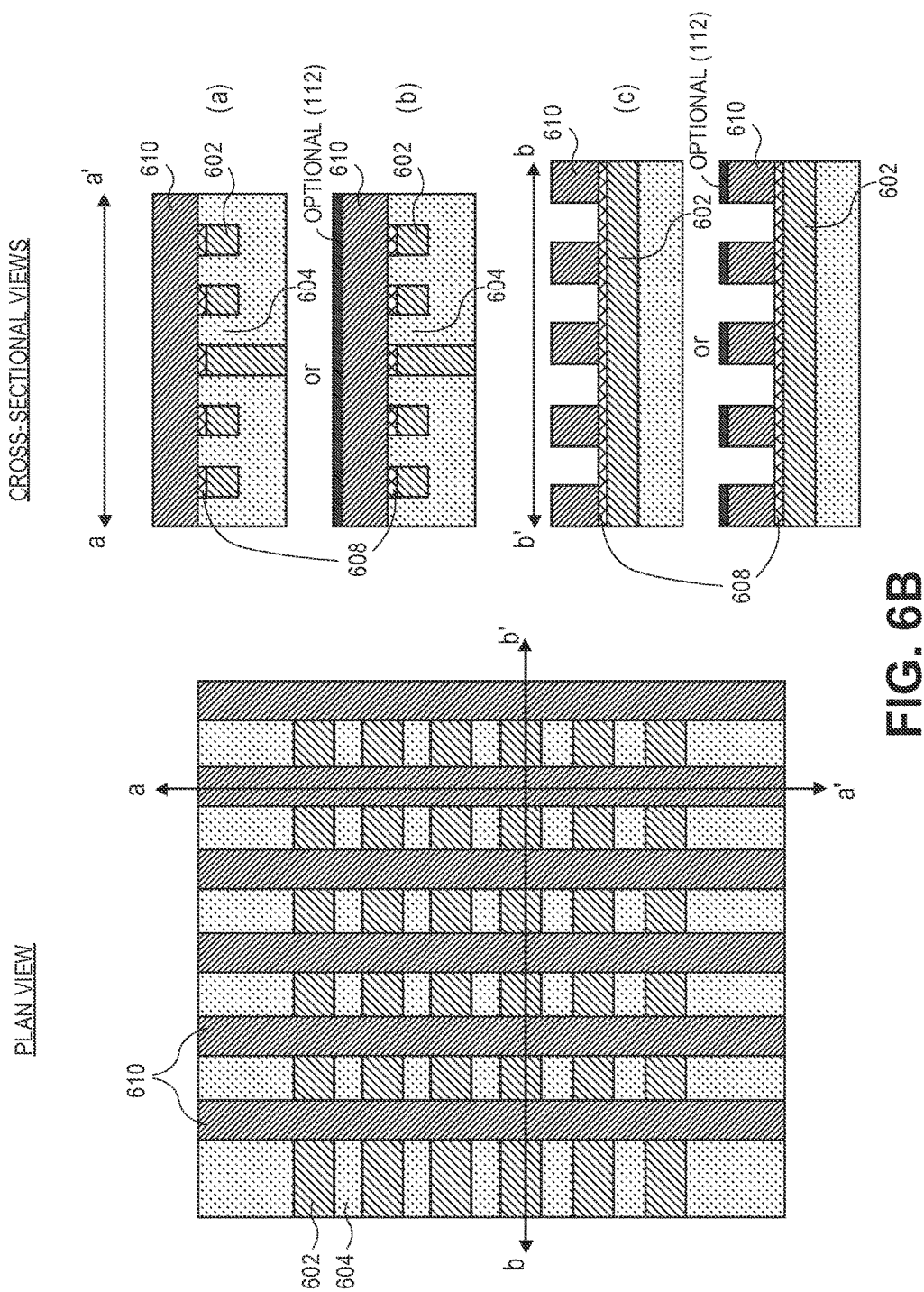

FIG. 6B illustrates a plan view and corresponding cross-sectional views of the structure of FIG. 6A following formation of interlayer dielectric (ILD) lines 610 above the structure of FIG. 6A, in accordance with an embodiment of the present invention. Referring to the plan view and corresponding cross-sectional views (a) and (c) taken along axes a-a' and c-c', respectively, the ILD lines 610 are formed in a grating structure perpendicular to the direction of underlying lines 604. In an embodiment, a blanket film of the material of lines 610 is deposited by chemical vapor deposition or like techniques. In an embodiment, the blanket film is then patterned using lithography and etch processing which may involve, e.g., spacer-based-quadruple-patterning (SBQP) or pitch quartering. It is to be understood that the grating pattern of lines 610 can be fabricated by numerous methods, including EUV and/or EBDW lithography, directed self-assembly, etc. As will be described in greater detail below, subsequent metal layer will thus be patterned in the orthogonal direction relative to the previous metal layer since the grating of lines 610 is orthogonal to the direction of the underlying structure. In one embodiment, a single 193 nm lithography mask is used with alignment/registration to the previous metal layer 602 (e.g., grating of lines 610 aligns to the previous layer 'plug' pattern in X and to the previous metal grating in Y). Referring to cross-sectional structures (b) and (d), a hardmask 612 may be formed on, or retained following patterning of, dielectric lines 610. The hardmask 612 can be used to protect lines 610 during subsequent patterning steps. As described in greater detail below, the formation of lines 610 in a grating pattern exposes regions of the previous metal lines 602 and previous ILD lines 604 (or corresponding hardmask layers on 602/604). The exposed regions correspond to all possible future via locations where metal is exposed. In one embodiment, the previous layer metal layer (e.g., lines 602 with the second or third row transition metal capping layer 608) is protected, labeled, brushed, etc. at this point in the process flow.

Figure 6C:
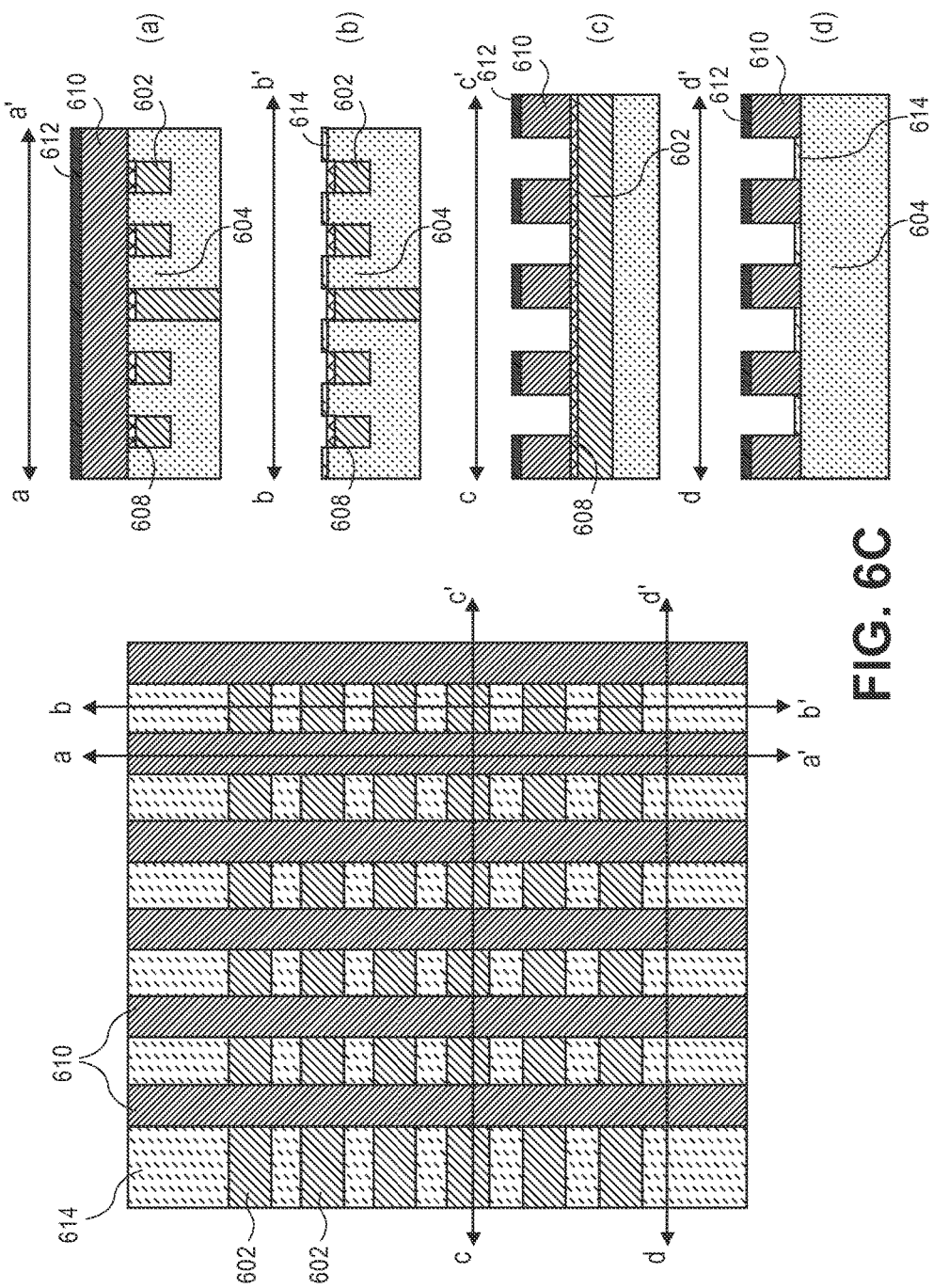

FIG. 6C illustrates a plan view and corresponding cross-sectional views of the structure of Figure B following selective differentiation all of the potential via locations from all of the plug locations, in accordance with an embodiment of the present invention. Referring to the plan view and corresponding cross-sectional views (a)-(d) taken along axes, a-a', b-b', c-c' and d-d', respectively, following formation of ILD lines 610, a surface modification layer 614 is formed on exposed regions of the underlying ILD lines 604. In an embodiment, surface modification layer 614 is a dielectric layer. In an embodiment, surface modification layer 614 is formed by a selective bottom-up growth approach. In one such embodiment, the bottom-up growth approach involves a directed self-assembly (DSA) brush coat that has one polymer component which assembles preferentially on the underlying ILD lines 604 or, alternatively, on the second or third row transition metal capping layer 608 of the metal lines 602.

FIG. 6D1 illustrates a plan view and corresponding cross-sectional views of the structure of FIG. 6C following differential polymer addition to the exposed portions of underlying metal and ILD lines of FIG. 6C, in accordance with an embodiment of the present invention. Referring to the plan view and corresponding cross-sectional views (a)-(d) taken along axes, a-a', b-b', c-c' and d-d', respectively, directed self-assembly (DSA) or selective growth on exposed portions of the underlying second or third row transition metal capping layer 608/ILD 608/604 grating is used to form intervening lines 616 with alternating polymers or alternating polymer components in between the ILD lines 610. For example, as shown, polymer 616A (or polymer component 616A) is formed on or above the exposed portions of interlayer dielectric (ILD) lines 604 of FIG. 6C, while polymer 616B (or polymer component 616B) is formed on or above the exposed portions of the second or third row transition metal capping layer 608 of the metal lines 602 of FIG. 6C. Although polymer 616A is formed on or above the surface modification layer 614 described in association with FIG. 6C (see cross-sectional views (b) and (d) of FIG. 6D1), it is to be understood that, in other embodiments, the surface modification layer 614 can be omitted and the alternating polymers or alternating polymer components can instead be formed directly in the structure described in association with FIG. 6B.

Referring again to FIG. 6D1, in an embodiment, once the surface of the underlying structure (e.g., structure 600 of FIG. 6A) has been prepared (e.g., such as the structure of FIG. 6B or the structure of FIG. 6C) or is used directly, a 50-50 diblock copolymer, such as polystyrene-polymethyl methacrylate (PS-PMMA), is coated on the substrate and annealed to drive self-assembly, leading to the polymer 616A/polymer 616B layer 616 of FIG. 6D1. In one such embodiment, with appropriate surface energy conditions, the block copolymers segregate based on the underlying material exposed between ILD lines 610. For example, in a specific embodiment, polystyrene aligns selectively to the exposed portions of the second or third row transition metal capping layer 608 of the underlying metal lines 602. Meanwhile, the polymethyl methacrylate aligns selectively to the exposed portions of ILD lines 604.

Thus, in an embodiment, the underlying metal and ILD grid, as exposed between ILD lines 610 is recreated in the block co-polymer (BCP, i.e., polymer 616A/polymer 616B). This can particularly be so if the BCP pitch is commensurate with the underlying grating pitch. The polymer grid (polymer 616A/polymer 616B) is, in one embodiment, robust against certain small deviations from a perfect grid. For example, if small plugs effectively place an oxide or like material where a perfect grid would have metal, a perfect polymer 616A/polymer 616B grid can still be achieved. However, since the ILD lines grating is, in one embodiment, an idealized grating structure, with no metal disruptions of the ILD backbone, it may be necessary to render the ILD surface neutral since both types of polymer (616A and 616B) will, in such an instance, be exposed to ILD like material while only one type is exposed to metal.

In an embodiment, the thickness of the coated polymer (polymer 616A/polymer 616B) is approximately the same as, or slightly thicker than, the ultimate thickness of an ILD ultimately formed in its place. In an embodiment, as described in greater detail below, the polymer grid is formed not as an etch resist, but rather as scaffolding for ultimately growing a permanent ILD layer there around. As such, the thickness of the polymer 616 (polymer 616A/polymer 616B) can be important since it may be used to define the ultimate thickness of a subsequently formed permanent ILD layer. That is, in one embodiment, the polymer grating shown in FIG. 6D1 is eventually replaced with an ILD grating of roughly the same thickness.

In an embodiment, as mentioned above, the grid of polymer 616A/polymer 616B of FIG. 6D1 is a block copolymer. In one such embodiment, the block copolymer molecule is a polymeric molecule formed of a chain of covalently bonded monomers. In a block copolymer, there are at least two different types of monomers, and these different types of monomers are primarily included within different blocks or contiguous sequences of monomers. The illustrated block copolymer molecule includes a block of polymer 616A and a block of polymer 616B. In an embodiment, the block of polymer 616A includes predominantly a chain of covalently linked monomer A (e.g., A-A-A-A-A . . . ), whereas the block of polymer 616B includes predominantly a chain of covalently linked monomer B (e.g., B-B-B-B-B . . . ). The monomers A and B may represent any of the different types of monomers used in block copolymers known in the arts. By way of example, the monomer A may represent monomers to form polystyrene, and the monomer B may represent monomers to form poly(methyl methacrylate) (PMMA), although the scope of the invention is not so limited. In other embodiments, there may be more than two blocks. Moreover, in other embodiments, each of the blocks may include different types of monomers (e.g., each block may itself be a copolymer). In one embodiment, the block of polymer 616A and the block of polymer 616B are covalently bonded together. The block of polymer 616A and the block of polymer 616B may be of approximately equal length, or one block may be significantly longer than the other.

Typically, the blocks of block copolymers (e.g., the block of polymer 616A and the block of polymer 616B) may each have different chemical properties. As one example, one of the blocks may be relatively more hydrophobic (e.g., water repelling) and the other may be relatively more hydrophilic (water attracting). At least conceptually, one of the blocks may be relatively more similar to oil and the other block may be relatively more similar to water. Such differences in chemical properties between the different blocks of polymers, whether a hydrophilic-hydrophobic difference or otherwise, may cause the block copolymer molecules to self-assemble. For example, the self-assembly may be based on microphase separation of the polymer blocks. Conceptually, this may be similar to the phase separation of oil and water which are generally immiscible. Similarly, differences in hydrophilicity between the polymer blocks (e.g., one block is relatively hydrophobic and the other block is relatively hydrophilic), may cause a roughly analogous microphase separation where the different polymer blocks try to "separate" from each other due to chemical dislike for the other.

However, in an embodiment, since the polymer blocks are covalently bonded to one another, they cannot completely separate on a macroscopic scale. Rather, polymer blocks of a given type may tend to segregate or conglomerate with polymer blocks of the same type of other molecules in extremely small (e.g., nano-sized) regions or phases. The particular size and shape of the regions or microphases generally depends at least in part upon the relative lengths of the polymer blocks. In an embodiment, by way of example (as shown in FIG. 6D1), in two block copolymers, if the blocks are approximately the same length, a grid like pattern of alternating polymer 616A lines and polymer 616B lines is generated. In another embodiment (not shown), in two block copolymers, if one of the blocks is longer than the other, but not too much longer than the other, columnar structures may formed. In the columnar structures, the block copolymer molecules may align with their shorter polymer blocks microphase separated into the interior of the columns and their longer polymer blocks extending away from the columns and surrounding the columns. For example, if the block of polymer 616A were longer than the block of polymer 616B, but not too much longer, columnar structures may formed in which many block copolymer molecules align with their shorter blocks of polymer 616B forming columnar structures surrounded by a phase having the longer blocks of polymer 616A. When this occurs in an area of sufficient size, a two-dimensional array of generally hexagonally-packed columnar structures may be formed.

In an embodiment, the polymer 616A/polymer 616B grating is first applied as an unassembled block copolymer layer portion that includes a block copolymer material applied, e.g., by brush or other coating process. The unassembled aspect refers to scenarios where, at the time of deposition, the block copolymer has not yet substantially phase separated and/or self-assembled to form nanostructures. In this unassembled form, the block polymer molecules are relatively highly randomized, with the different polymer blocks relatively highly randomly oriented and located, which is in contrast to the assembled block copolymer layer portion discussed in association with the resulting structure of FIG. 6D1. The unassembled block copolymer layer portion may be applied in a variety of different ways. By way of example, the block copolymer may be dissolved in a solvent and then spin coated over the surface. Alternatively, the unassembled block copolymer may be spray coated, dip coated, immersion coated, or otherwise coated or applied over the surface. Other ways of applying block copolymers, as well as other ways known in the arts for applying similar organic coatings, may potentially be used. Then, the unassembled layer may form an assembled block copolymer layer portion, e.g., by microphase separation and/or self-assembly of the unassembled block copolymer layer portion. The microphase separation and/or self-assembly occurs through rearrangement and/or repositioning of the block copolymer molecules, and in particular to rearrangement and/or repositioning of the different polymer blocks of the block copolymer molecules.

In one such embodiment, an annealing treatment may be applied to the unassembled block copolymer in order to initiate, accelerate, increase the quality of, or otherwise promote microphase separation and/or self-assembly. In some embodiments, the annealing treatment may include a treatment that is operable to increase a temperature of the block copolymer. One example of such a treatment is baking the layer, heating the layer in an oven or under a thermal lamp, applying infrared radiation to the layer, or otherwise applying heat to or increasing the temperature of the layer. The desired temperature increase will generally be sufficient to significantly accelerate the rate of microphase separation and/or self-assembly of the block polymer without damaging the block copolymer or any other important materials or structures of the integrated circuit substrate. Commonly, the heating may range between about 50° C. to about 300° C., or between about 75° C. to about 250° C., but not exceeding thermal degradation limits of the block copolymer or integrated circuit substrate. The heating or annealing may help to provide energy to the block copolymer molecules to make them more mobile/flexible in order to increase the rate of the microphase separation and/or improve the quality of the microphase separation. Such microphase separation or rearrangement/repositioning of the block copolymer molecules may lead to self-assembly to form extremely small (e.g., nano-scale) structures. The self-assembly may occur under the influence of surface energy, molecular affinities, and other surface-related and chemical-related forces.

In any case, in some embodiments, self-assembly of block copolymers, whether based on hydrophobic-hydrophilic differences or otherwise, may be used to form extremely small periodic structures (e.g., precisely spaced nano-scale structures or lines). In some embodiments, they may be used to form nano-scale lines or other nano-scale structures that can ultimately be used to form via and openings. In some embodiments, directed self-assembly of block copolymers may be used to form vias that are self-aligned with interconnects, as described in greater detail below.

Referring again to FIG. 6D1, in an embodiment, for a DSA process, in addition to direction from the underlying ILD/second or third row transition metal capping layer 604/608 surfaces the growth process can be affected by the sidewalls of the material of ILD lines 610. As such, in one embodiment, DSA is controlled through graphoepitaxy (from the sidewalls of lines 610) and chemoepitaxy (from the underlying exposed surface characteristics). Constraining the DSA process both physically and chemically can significantly aid the process from a defectivity standpoint. The resulting polymers 616A/616B have fewer degrees of freedom and are fully constrained in all directions through chemical (e.g., underlying ILD or the second or third row transition metal capping layer 608 of the metal lines, or surface modifications made thereto by, for example, a brush approach) and physical (e.g., from the trenches formed between the ILD lines 610).

In an alternative embodiment, a selective growth process is used in place of a DSA approach. FIG. 6D2 illustrates a cross-sectional view of the structure of FIG. 6B following selective material deposition on the exposed portions of underlying metal and ILD lines, in accordance with another embodiment of the present invention. Referring to FIG. 6D2, a first material type 800 is grown above exposed portions of the underlying ILD lines 604. A second, different, material type 802 is grown above exposed portions of the second or third row transition metal capping layer 608 of the underlying metal lines 602. In an embodiment, the selective growth is achieved by a dep-etch-dep-etch approach for each of the first and second materials, resulting in a plurality of layers of each of the materials, as depicted in FIG. 6D2. Such an approach may be favorable versus conventional selective growth techniques which can form "mushroom-top" shaped films. The mushroom topping film growth tendency can be reduced through an alternating deposition/etch/deposition (dep-etch-dep-etch) approach. In another embodiment, a film is deposited selectively over the metal followed by a different film selectively over the ILD (or vice versa) and repeated numerous times creating a sandwich-like stack. In another embodiment, both materials are grown simultaneously in a reaction chamber (e.g., by a CVD style process) that grows selectively on each exposed region of the underlying substrate.

Figure 6E:
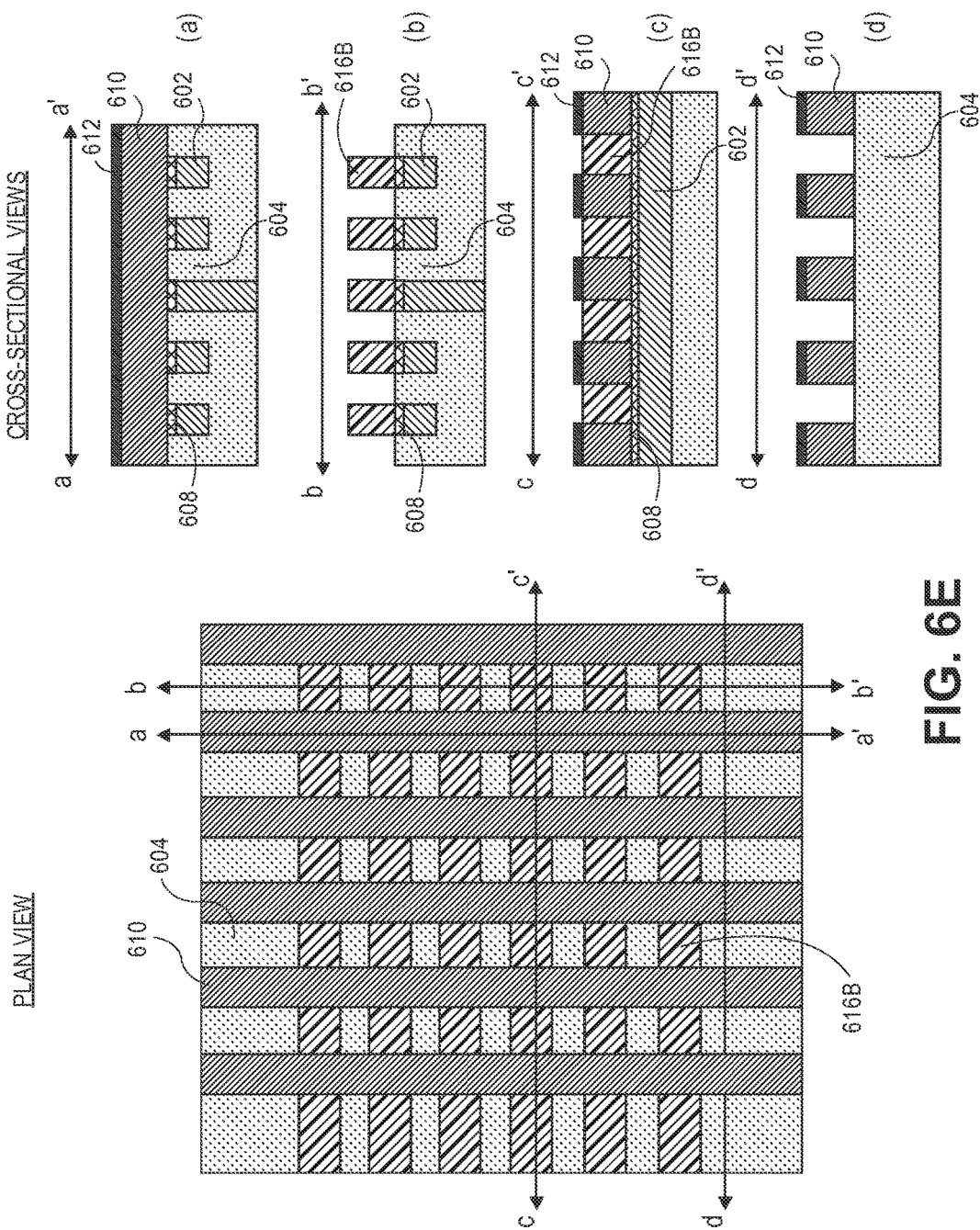

FIG. 6E illustrates a plan view and corresponding cross-sectional views of the structure of FIG. 6D1 following removal of one species of polymer, in accordance with an embodiment of the present invention. Referring to the plan view and corresponding cross-sectional views (a)-(d) taken along axes, a-a', b-b', c-c' and d-d', respectively, polymer or polymer portion 616A is removed to re-expose the ILD lines 604 (or hardmask or cap layers formed on the ILD lines 604), while polymer or polymer portion 616B is retained above the second or third row transition metal capping layer 608 of the metal lines 602. In an embodiment, a deep ultra-violet (DUV) flood expose followed by a wet etch or a selective dry etch is used to selectively remove polymer 616A. It is to be understood that, instead of first removal of the polymer from the ILD lines 604 (as depicted), removal from the second or third row transition metal capping layer 608 of the metal lines 602 may instead be first performed. Alternatively, a dielectric film is selectively grown over the region, and a mixed scaffolding is not used.

Figure 6F:
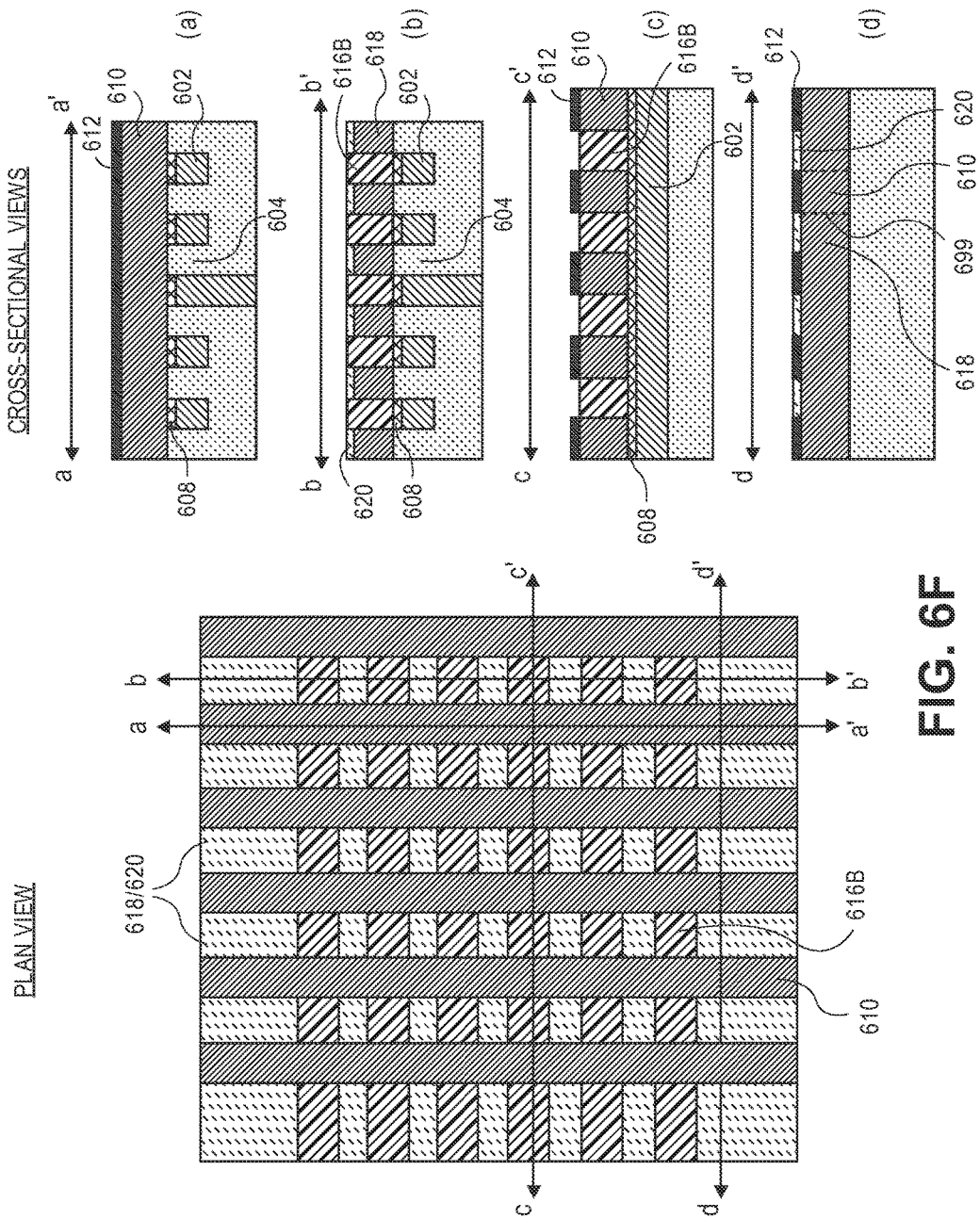

FIG. 6F illustrates a plan view and corresponding cross-sectional views of the structure of FIG. 6E following formation of an ILD material in the locations opened upon removal of the one species of polymer, in accordance with an embodiment of the present invention. Referring to the plan view and corresponding cross-sectional views (a)-(d) taken along axes, a-a', b-b', c-c' and d-d', respectively, the exposed regions of underlying ILD lines 604 are filled with a permanent interlayer dielectric (ILD) layer 618. As such, the open spaces between all possible via positions are filled with an ILD layer 618 includes a hardmask layer 620 disposed thereon, as depicted in the plan view and in the cross-sectional views (b) and (d) of FIG. 6F. It is to be understood that the material of ILD layer 618 need not be the same material as ILD lines 610. In an embodiment, the ILD layer 618 is formed by a deposition and polish process. In the case where ILD layer 618 is formed with an accompanying hardmask layer 620, a special ILD fill material may be used (e.g., polymer encapsulated nanoparticles of ILD that fills holes/trenches). In such a case, a polish operation may not be necessary.

Referring again to FIG. 6F, in an embodiment, the resulting structure includes a uniform ILD structure (ILD lines 610+ILD layer 618), and the locations of all possible plugs are covered in hardmask 620 and all possible vias are in areas of polymer 616B. In one such embodiment, ILD lines 610 and ILD layer 618 are composed of a same material. In another such embodiment, ILD lines 610 and ILD layer 618 are composed of different ILD materials. In either case, in a specific embodiment, a distinction such as a seam between the materials of ILD lines 610 and ILD layer 618 may be observed in the final structure. Exemplary seams 699 are shown in FIG. 6F for illustrative purposes.

FIG. 6G illustrates a plan view and corresponding cross-sectional views of the structure of FIG. 6F following via patterning, in accordance with an embodiment of the present invention. Referring to the plan view and corresponding cross-sectional views (a)-(d) taken along axes, a-a', b-b', c-c' and d-d', respectively, via locations 622A, 622B and 622C are opened by removal of polymer 616B in select locations. In an embodiment, selective via location formation is accomplished by using a lithographic technique. In one such embodiment, polymer 616B is globally removed with an ash and refilled with photoresist. The photoresist may be highly sensitive and have a large acid diffusion and aggressive deprotection or crosslinking (depending on resist tone) because the latent image is confined in both directions by ILD (e.g., by ILD lines 610 and ILD layer 618). The resist serves as a digital switch to turn "on" or "off" depending whether a via is required in a particular location or not. Ideally, the photoresist can be used to fill the holes only, without spilling over. In an embodiment, the via locations 622A, 622B and 622C are fully confined with the process such that line edge or width roughness (LWR) and line collapse and/or reflection is mitigated if not eliminated. In an embodiment, low doses are used with EUV/EBDW and increase runrate significantly. In one embodiment, an additional advantage with the use of EBDW is that only a single shot type/size that can increase runrate by significantly reducing the number of apertures required as well as lowering the dose that needs to be delivered. In a case that 193 nm immersion lithography is used, in an embodiment, the process flow confines the via locations in both directions such the size of the via that actually is patterned is twice the size of the actual via on the wafer (e.g., assuming 1:1 line/space patterns). Alternatively, the via locations can be selected in the reverse tone where the vias that need to be retained are protected with photoresist and the remaining sites are removed and later filled with ILD. Such an approach can allow a single metal fill/polish process at the end of the patterning flow rather than two separate metal deposition steps.

Figure 6H:
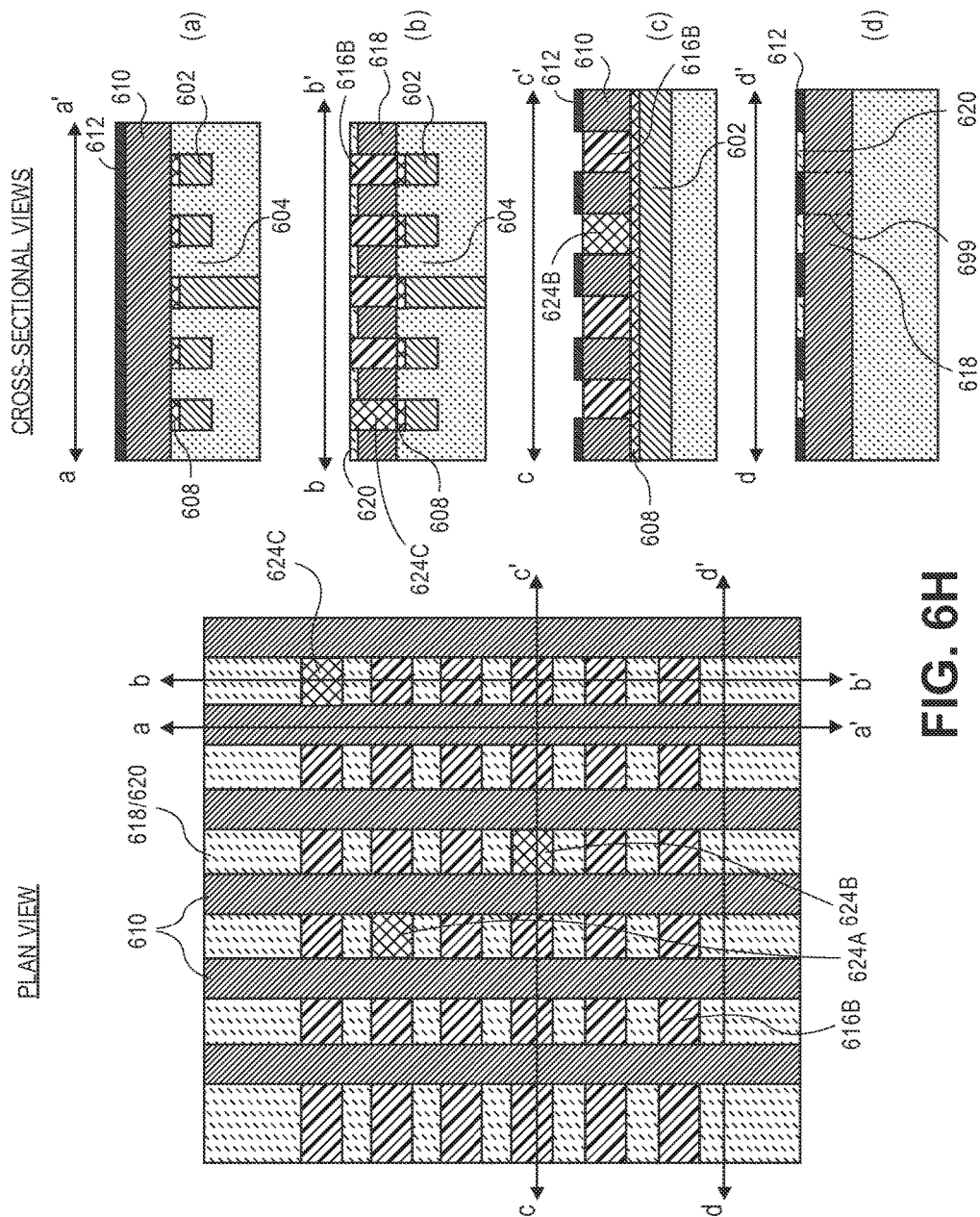

FIG. 6H illustrates a plan view and corresponding cross-sectional views of the structure of FIG. 6G following via formation. In an embodiment via formation is effected using deposition of a second or third row transition metal formed using a complex such as one of the complexes (a)-(d) of FIG. 5 or their isomers in an atomic layer deposition or a chemical vapor deposition processing scheme. In other embodiments, however, conventional electroplating or electroless plating is used.

Referring again to the plan view and corresponding cross-sectional views (a)-(d) of FIG. 6H taken along axes, a-a', b-b', c-c' and d-d', respectively, via locations 622A, 622B and 622C are filled with metal to form vias 624A, 624B and 624C, respectively. In an embodiment, via locations 622A, 622B and 622C are filled (or at least seeded) using an inherently selective metal deposition process as described above. In one such embodiment, an inherently selective second or third row transition metal ALD/CVD process is used to deposit metal in via locations 622A, 622B and 622C selectively against all other exposed dielectric materials. As such, in accordance with an embodiment of the present invention, via locations 622A, 622B and 622C are filled without using a conventional metal over-fill and polishing process.

Figure 6I:
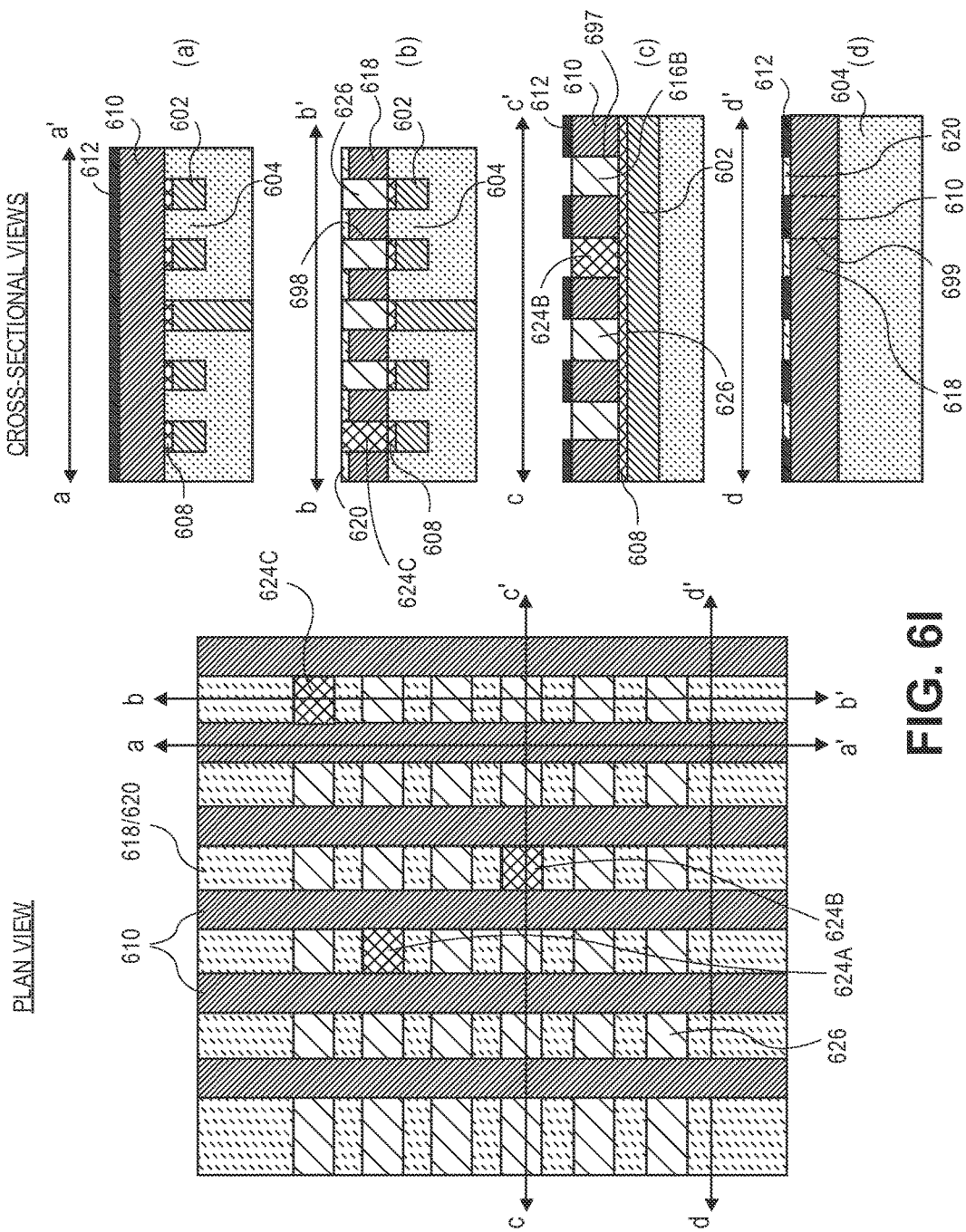

FIG. 6I illustrates a plan view and corresponding cross-sectional views of the structure of FIG. 6H following removal of the second species of polymer and replacement with an ILD material, in accordance with an embodiment of the present invention. Referring to the plan view and corresponding cross-sectional views (a)-(d) taken along axes, a-a', b-b', c-c' and d-d', respectively, remaining polymer or polymer portion 616B (e.g., where vias locations have not been selected) is removed to re-expose the metal lines 602. Subsequently, an ILD layer 626 is formed in the locations where the remaining polymer or polymer portion 616B was removed, as depicted in FIG. 6I.

Referring again to FIG. 6I, in an embodiment, the resulting structure includes a uniform ILD structure (ILD lines 610+ILD layer 618+ILD layer 626), and the locations of all possible plugs are covered in hardmask 620. In one such embodiment, ILD lines 610, ILD layer 618 and ILD layer 626 are composed of a same material. In another such embodiment, two of ILD lines 610, ILD layer 618 and ILD layer 626 are composed of a same material and the third is composed of a different ILD material. In yet another such embodiment, all of ILD lines 610, ILD layer 618 and ILD layer 626 are composed of a different ILD material with respect to one another. In any case, in a specific embodiment, a distinction such as a seam between the materials of ILD lines 610 and ILD layer 626 may be observed in the final structure. Exemplary seams 697 are shown in FIG. 6I for illustrative purposes. Likewise, a distinction such as a seam between the materials of ILD layer 618 and ILD layer 626 may be observed in the final structure. Exemplary seams 698 are shown in FIG. 6I for illustrative purposes.

Figure 6J:
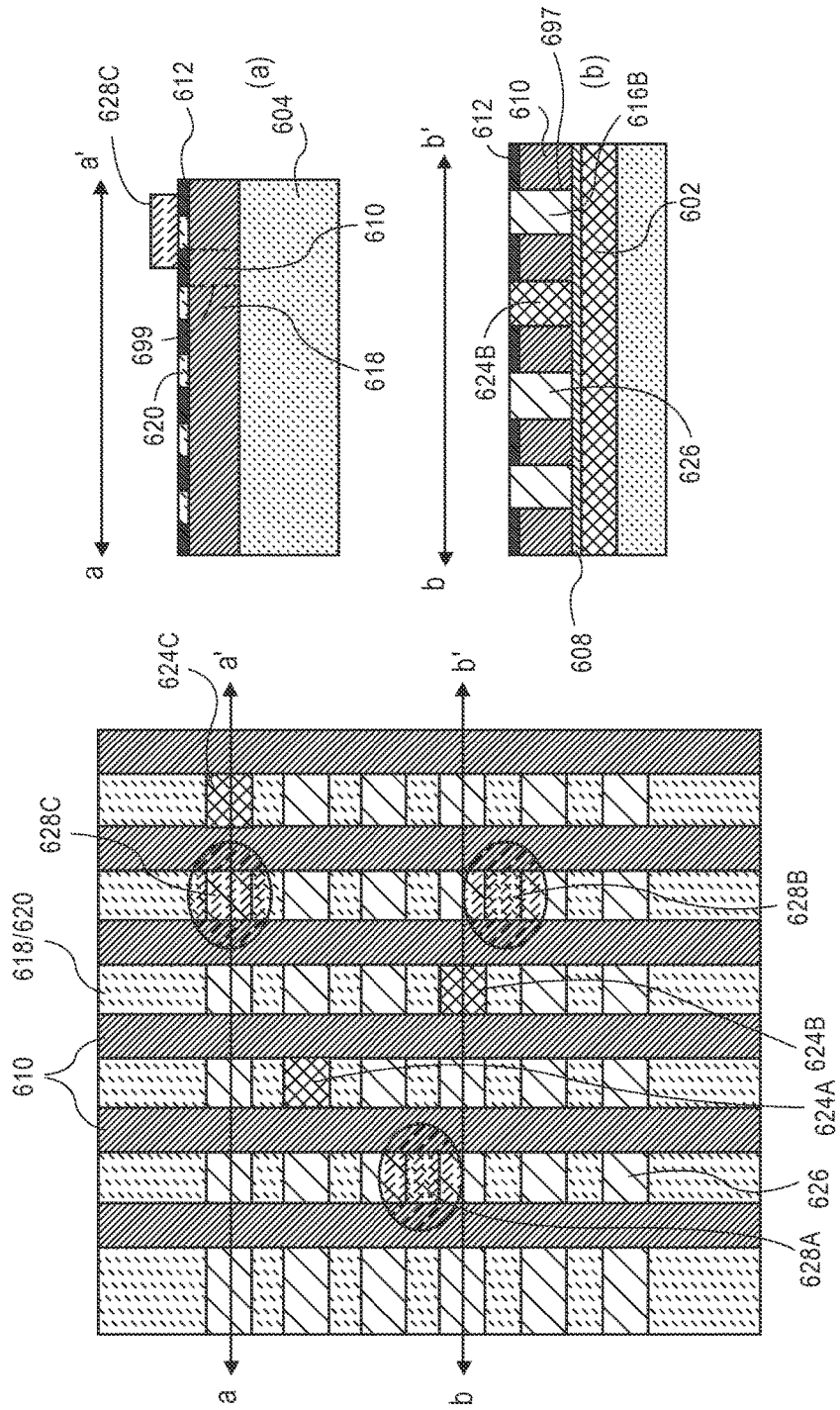

FIG. 6J illustrates a plan view and corresponding cross-sectional views of the structure of FIG. 6I following patterning of a resist or mask in selected plug locations, in accordance with an embodiment of the present invention. Referring to the plan view and corresponding cross-sectional views (a) and (b) taken along axes, a-a' and b-b', respectively, plug positions 628A, 628B and 628C are preserved by forming a mask or resist layer over those locations. Such preservation patterning may be referred to as metal end-to-end lithographic patterning, wherein plug positions are determined where breaks in subsequently formed metal lines are required. It is to be understood that since the plug locations can only be in those locations where ILD layer 618/hardmask 620 are positioned, plugs can occur over the previous layer ILD lines 604. In an embodiment, the patterning is achieved by using a lithography operation (e.g., EUV, EBDW or immersion 193 nm). In an embodiment, the process illustrated in FIG. 6J, demonstrates use of a positive tone patterning process where the regions where spaces between metal need to occur are preserved. It is to be understood that, in another embodiment, it is also possible to open holes instead and reverse the tone of the process.

Figure 6K:
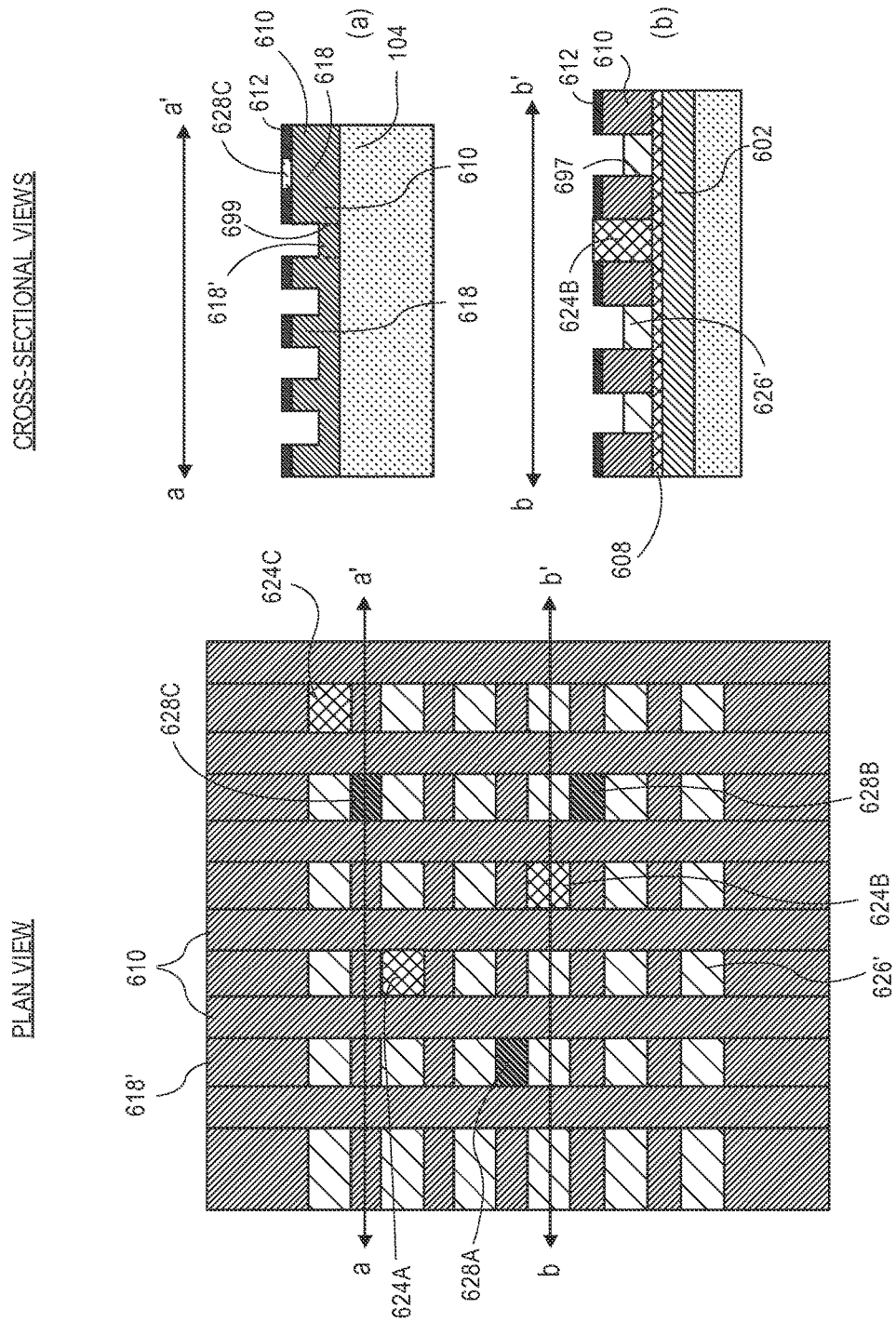

FIG. 6K illustrates a plan view and corresponding cross-sectional views of the structure of FIG. 6J following hardmask removal and ILD layer recessing, in accordance with an embodiment of the present invention. Referring to the plan view and corresponding cross-sectional views (a) and (b) taken along axes, a-a' and b-b', respectively, hardmask 620 is removed and ILD layer 618 and ILD layer 626 are recessed to form recessed ILD layer 618' and recessed ILD layer 626', respectively, by etching of these layers below their original uppermost surfaces. It is to be understood that the recessing of ILD layer 618 and ILD layer 626 is performed without etching or recessing ILD lines 610. The selectivity may be achieved by use of a hardmask layer 612 on the ILD lines (as depicted in cross-sectional views (a) and (b)). Alternatively, in a case that the ILD lines 610 are composed of an ILD material different from the material of ILD layer 618 and ILD layer 626, a selective etch may be used even in the absence of a hardmask 612. The recessing of ILD layer 618 and ILD layer 626 is to provide locations for the second level of metal lines, as isolated by ILD lines 610, as described below. The extent or depth of the recess is, in one embodiment, selected based on the desired ultimate thickness of the metal lines formed thereon. It is to be understood that the ILD layer 618 in the plug locations 628A, 628B and 628C is not recessed.

Figure 6L:
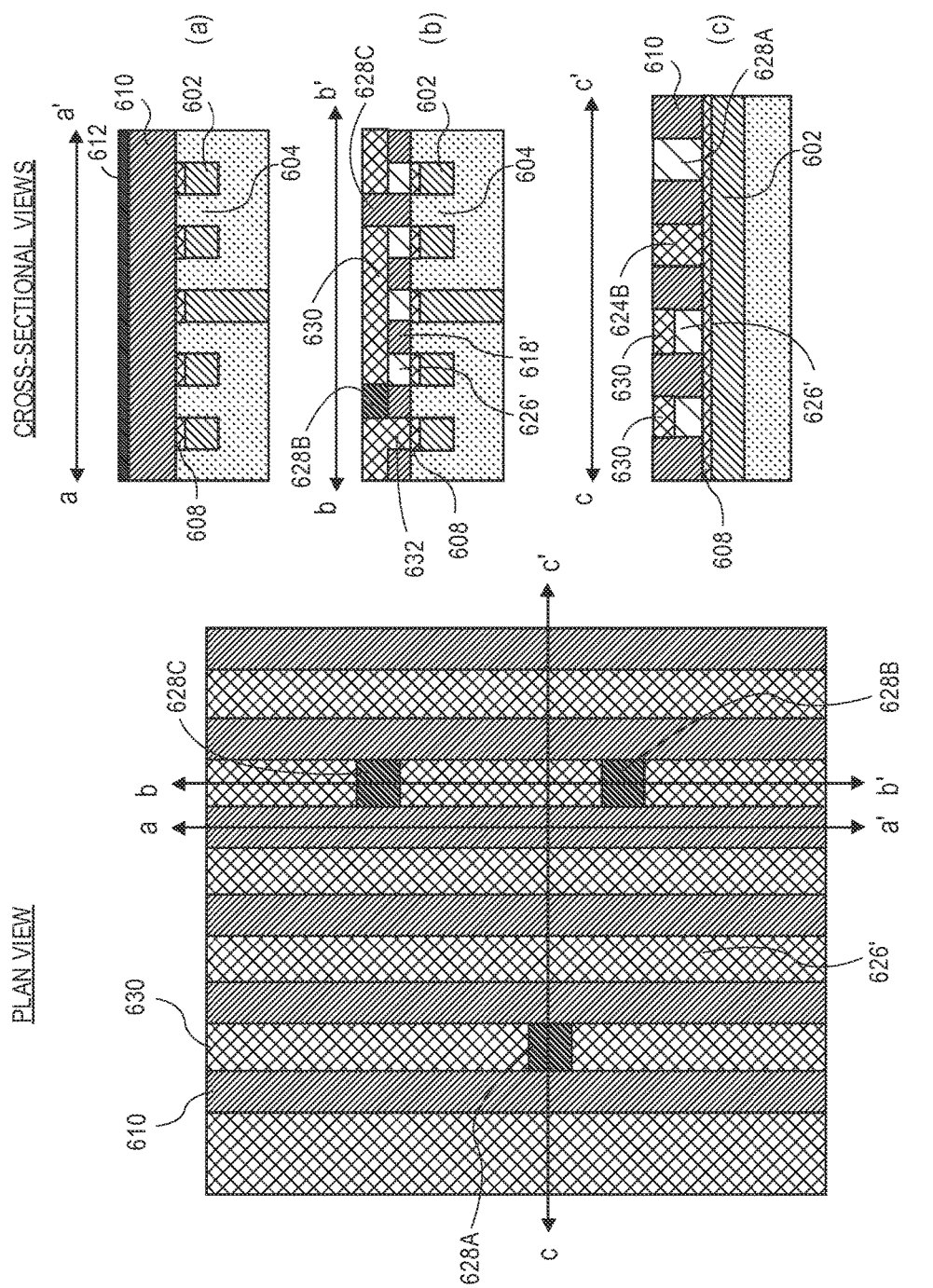

FIG. 6L illustrates a plan view and corresponding cross-sectional views of the structure of FIG. 6K following metal line formation, in accordance with an embodiment of the present invention. Referring to the plan view and corresponding cross-sectional views (a), (b) and (c) taken along axes, a-a', b-b' and c-c', respectively, metal for forming metal interconnect lines is formed conformally above the structure of FIG. 6K. The metal is then planarized, e.g., by CMP, to provide metal lines 630, which are confined to locations above recessed ILD layer 618' and recessed ILD layer 626'. The metal lines 630 are coupled with underlying metal lines 602 through the predetermined via locations 624A, 624B and 624C (624B is shown in cross-sectional view (c); note that for illustrative purposes, another via 632 is depicted directly adjacent plug 628B in cross-sectional view (b) even though this is inconsistent with the previous figures). The metal lines 630 are isolated from one another by ILD lines 610 and are disrupted or broken-up by the preserved plugs 628A, 628B and 628C. Any hardmask remaining on the plug locations and/or on the ILD lines 610 may be removed at this portion of the process flow, as depicted in FIG. 6L. The metal (e.g., copper and associated barrier and seed layers) deposition and planarization process to form metal lines 630 may be that typically used for standard back end of line (BEOL) single or dual damascene processing. In an embodiment, in subsequent fabrication operations, the ILD lines 610 may be removed to provide air gaps between the resulting metal lines 630. In one embodiment, metal line formation is effected using deposition of a second or third row transition metal formed using a complex such as one of the complexes (a)-(d) of FIG. 5 or their isomers in an atomic layer deposition or a chemical vapor deposition processing scheme. In other embodiments, conventional electroplating or electroless plating is used.

The structure of FIG. 6L may subsequently be used as a foundation for forming subsequent metal line/via and ILD layers. Alternatively, the structure of FIG. 6L may represent the final metal interconnect layer in an integrated circuit. It is to be understood that the above process operations may be practiced in alternative sequences, not every operation need be performed and/or additional process operations may be performed. Furthermore, although the above process flow focused on applications of directed self-assembly (DSA), selective growth processes may be used instead in one or more locations of the process flow. In any case, the resulting structures enable fabrication, by selective metal deposition (e.g., inherently selective deposition of a second or third row transition metal layer), of vias that are directly centered on underlying metal lines. That is, the vias may be wider than, narrower than, or the same thickness as the underlying metal lines, e.g., due to non-perfect selective etch processing. Nonetheless, in an embodiment, the centers of the vias are directly aligned (match up) with the centers of the metal lines. As such, in an embodiment, offset due to conventional lithograph/dual damascene patterning that must otherwise be tolerated, is not a factor for the resulting structures described herein.

In another aspect, one or more embodiments described herein are directed to fabricating semiconductor devices, such as for PMOS and NMOS device fabrication. As an example of a completed device, FIGS. 7A and 7B illustrate a cross-sectional view and a plan view (taken along the a-a' axis of the cross-sectional view), respectively, of a non-planar semiconductor device having a metal gate fill layer formed using an inherently selective precursor for deposition of a second or third row transition metal (e.g., tungsten or ruthenium) thin film, in accordance with an embodiment of the present invention.

Figure 7A:
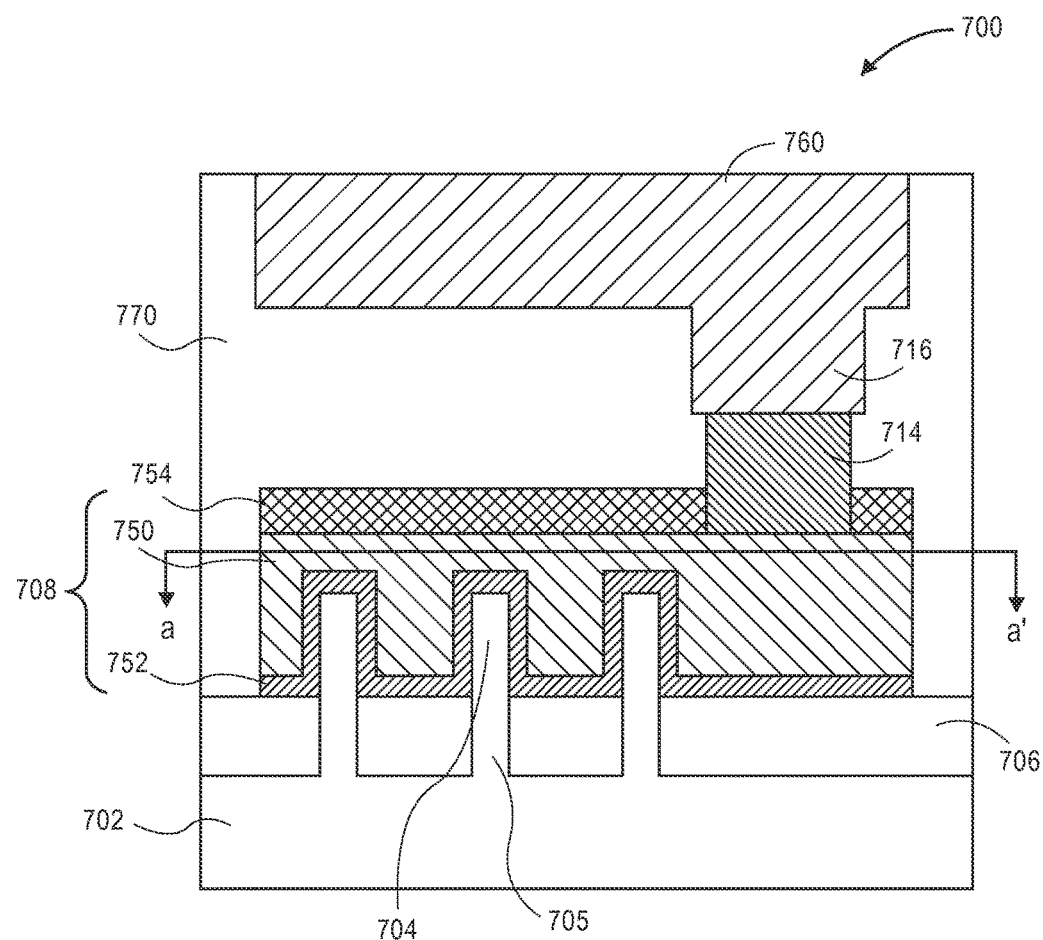
FIG. 7A illustrates a cross-sectional view of a non-planar semiconductor device having fins having a metal gate fill layer formed using an inherently selective precursor for deposition of a second or third row transition metal (e.g., tungsten or ruthenium) thin film, in accordance with an embodiment of the present invention.

Referring to FIG. 7A, a semiconductor structure or device 700 includes a non-planar active region (e.g., a fin structure including protruding fin portion 704 and sub-fin region 705) formed from substrate 702, and within isolation region 706. A gate line 708 is disposed over the protruding portions 704 of the non-planar active region as well as over a portion of the isolation region 706. As shown, gate line 708 includes a gate electrode 750 and a gate dielectric layer 752. In one embodiment, gate line 708 may also include a dielectric cap layer 754.l A gate contact 714, and overlying gate contact via 716 are also seen from this perspective, along with an overlying metal interconnect 760, all of which are disposed in inter-layer dielectric stacks or layers 770. Also seen from the perspective of FIG. 7A, the gate contact 714 is, in one embodiment, disposed over isolation region 706, but not over the non-planar active regions.

An embodiment described in greater detail below in association with gate stack formation involves formation of a second or third row transition metal layer for at least a portion of a metal gate electrode. Another embodiment described in greater detail below in association with gate contact or gate contact via formation involves formation of a second or third row transition metal layer for at least a portion of a gate contact or gate contact via.

Figure 7B:
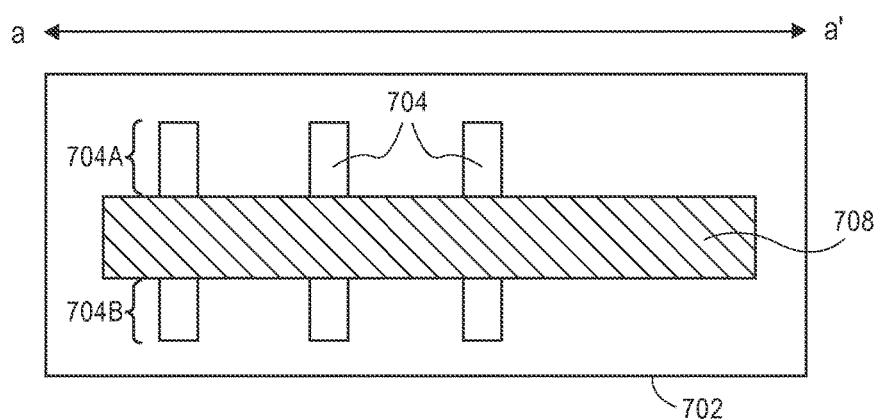
FIG. 7B illustrates a plan view taken along the a-a' axis of the semiconductor device of FIG. 7A, in accordance with an embodiment of the present invention.

Referring to FIG. 7B, the gate line 708 is shown as disposed over the protruding fin portions 704. Source and drain regions 704A and 704B of the protruding fin portions 704 can be seen from this perspective. In one embodiment, the source and drain regions 704A and 704B are doped portions of original material of the protruding fin portions 704. In another embodiment, the material of the protruding fin portions 704 is removed and replaced with another semiconductor material, e.g., by epitaxial deposition. In either case, the source and drain regions 704A and 704B may extend below the height of dielectric layer 706, i.e., into the sub-fin region 705.

In an embodiment, the semiconductor structure or device 700 is a non-planar device such as, but not limited to, a fin-FET or a tri-gate device. In such an embodiment, a corresponding semiconducting channel region is composed of or is formed in a three-dimensional body. In one such embodiment, the gate electrode stacks of gate lines 708 surround at least a top surface and a pair of sidewalls of the three-dimensional body.

Substrate 702 may be composed of a semiconductor material that can withstand a manufacturing process and in which charge can migrate. In an embodiment, substrate 702 is a bulk substrate composed of a crystalline silicon, silicon/germanium or germanium layer doped with a charge carrier, such as but not limited to phosphorus, arsenic, boron or a combination thereof, to form active region 704. In one embodiment, the concentration of silicon atoms in bulk substrate 702 is greater than 97%. In another embodiment, bulk substrate 702 is composed of an epitaxial layer grown atop a distinct crystalline substrate, e.g. a silicon epitaxial layer grown atop a boron-doped bulk silicon mono-crystalline substrate. Bulk substrate 702 may alternatively be composed of a group III-V material. In an embodiment, bulk substrate 702 is composed of a III-V material such as, but not limited to, gallium nitride, gallium phosphide, gallium arsenide, indium phosphide, indium antimonide, indium gallium arsenide, aluminum gallium arsenide, indium gallium phosphide, or a combination thereof. In one embodiment, bulk substrate 702 is composed of a III-V material and the charge-carrier dopant impurity atoms are ones such as, but not limited to, carbon, silicon, germanium, oxygen, sulfur, selenium or tellurium.

Isolation region 706 may be composed of a material suitable to ultimately electrically isolate, or contribute to the isolation of, portions of a permanent gate structure from an underlying bulk substrate or isolate active regions formed within an underlying bulk substrate, such as isolating fin active regions. For example, in one embodiment, the isolation region 706 is composed of a dielectric material such as, but not limited to, silicon dioxide, silicon oxy-nitride, silicon nitride, or carbon-doped silicon nitride.

Gate line 708 may be composed of a gate electrode stack which includes a gate dielectric layer 752 and a gate electrode layer 750. In an embodiment, the gate electrode of the gate electrode stack is composed of a metal gate and the gate dielectric layer is composed of a high-K material. For example, in one embodiment, the gate dielectric layer is composed of a material such as, but not limited to, hafnium oxide, hafnium oxy-nitride, hafnium silicate, lanthanum oxide, zirconium oxide, zirconium silicate, tantalum oxide, barium strontium titanate, barium titanate, strontium titanate, yttrium oxide, aluminum oxide, lead scandium tantalum oxide, lead zinc niobate, or a combination thereof. Furthermore, a portion of gate dielectric layer may include a layer of native oxide formed from the top few layers of the substrate 702. In an embodiment, the gate dielectric layer is composed of a top high-k portion and a lower portion composed of an oxide of a semiconductor material. In one embodiment, the gate dielectric layer is composed of a top portion of hafnium oxide and a bottom portion of silicon dioxide or silicon oxy-nitride.

In accordance with an embodiment of the present invention, at least a portion of a metal gate is formed using an inherently selective deposition process. In one such embodiment, a complex such as one of the complexes (a)-(d) of FIG. 5 or their isomers is used in an atomic layer deposition or a chemical vapor deposition processing scheme to deposit a second or third row transition metal layer. In one such embodiment, a complex such as one of the complexes (a)-(d) or their isomers is used to deposit a high purity tungsten layer by ALD or CVD. In another embodiment, a complex such as one of the complexes (a)-(d) or their isomers is used to deposit a high purity ruthenium layer by ALD or CVD. In an embodiment, the second or third row transition metal layer is used as a fill layer atop a workfunction metal layer of a metal gate electrode.

Spacers associated with the gate electrode stacks may be composed of a material suitable to ultimately electrically isolate, or contribute to the isolation of, a permanent gate structure from adjacent conductive contacts, such as self-aligned contacts. For example, in one embodiment, the spacers are composed of a dielectric material such as, but not limited to, silicon dioxide, silicon oxy-nitride, silicon nitride, or carbon-doped silicon nitride.

Gate contact 714 and overlying gate contact via 716 may be composed of a conductive material. In an embodiment, one or more of the contacts or vias are composed of a metal species. The metal species may be a pure metal, such as tungsten, nickel, or cobalt, or may be an alloy such as a metal-metal alloy or a metal-semiconductor alloy (e.g., such as a silicide material). In accordance with another embodiment of the present invention, at least a portion of a gate contact or gate contact via is formed using an inherently selective deposition process. In one such embodiment, a complex such as one of the complexes (a)-(d) of FIG. 5 or their isomers is used in an atomic layer deposition or a chemical vapor deposition processing scheme to deposit a second or third row transition metal layer. In one such embodiment, a complex such as one of the complexes (a)-(d) or their isomers is used to deposit a high purity tungsten layer by ALD or CVD. In another embodiment, a complex such as one of the complexes (a)-(d) or their isomers is used to deposit a high purity ruthenium layer by ALD or CVD.

In an embodiment (although not shown), providing structure 700 involves formation of a contact pattern which is essentially perfectly aligned to an existing gate pattern while eliminating the use of a lithographic step with exceedingly tight registration budget. In one such embodiment, this approach enables the use of intrinsically highly selective wet etching (e.g., versus conventionally implemented dry or plasma etching) to generate contact openings. In an embodiment, a contact pattern is formed by utilizing an existing gate pattern in combination with a contact plug lithography operation. In one such embodiment, the approach enables elimination of the need for an otherwise critical lithography operation to generate a contact pattern, as used in conventional approaches. In an embodiment, a trench contact grid is not separately patterned, but is rather formed between poly (gate) lines. For example, in one such embodiment, a trench contact grid is formed subsequent to gate grating patterning but prior to gate grating cuts.

Furthermore, the gate stack structure 708 may be fabricated by a replacement gate process. In such a scheme, dummy gate material such as polysilicon or silicon nitride pillar material, may be removed and replaced with permanent gate electrode material. In one such embodiment, a permanent gate dielectric layer is also formed in this process, as opposed to being carried through from earlier processing. In an embodiment, dummy gates are removed by a dry etch or wet etch process. In one embodiment, dummy gates are composed of polycrystalline silicon or amorphous silicon and are removed with a dry etch process including use of $SF_6$. In another embodiment, dummy gates are composed of polycrystalline silicon or amorphous silicon and are removed with a wet etch process including use of aqueous $NH_4OH$ or tetramethylammonium hydroxide. In one embodiment, dummy gates are composed of silicon nitride and are removed with a wet etch including aqueous phosphoric acid.

In an embodiment, one or more approaches described herein contemplate essentially a dummy and replacement gate process in combination with a dummy and replacement contact process to arrive at structure 700. In one such embodiment, the replacement contact process is performed after the replacement gate process to allow high temperature anneal of at least a portion of the permanent gate stack. For example, in a specific such embodiment, an anneal of at least a portion of the permanent gate structures, e.g., after a gate dielectric layer is formed, is performed at a temperature greater than approximately 600 degrees Celsius. The anneal is performed prior to formation of the permanent contacts.

Referring again to FIG. 7A, the arrangement of semiconductor structure or device 700 places the gate contact over isolation regions. Such an arrangement may be viewed as inefficient use of layout space. In another embodiment, however, a semiconductor device has contact structures that contact portions of a gate electrode formed over an active region. In general, prior to (e.g., in addition to) forming a gate contact structure (such as a via) over an active portion of a gate and in a same layer as a trench contact via, one or more embodiments of the present invention include first using a gate aligned trench contact process. Such a process may be implemented to form trench contact structures for semiconductor structure fabrication, e.g., for integrated circuit fabrication. In an embodiment, a trench contact pattern is formed as aligned to an existing gate pattern. By contrast, conventional approaches typically involve an additional lithography process with tight registration of a lithographic contact pattern to an existing gate pattern in combination with selective contact etches. For example, a conventional process may include patterning of a poly (gate) grid with separate patterning of contact features.

It is to be appreciated that not all aspects of the processes described above need be practiced to fall within the spirit and scope of embodiments of the present invention. For example, in one embodiment, dummy gates need not ever be formed prior to fabricating gate contacts over active portions of the gate stacks. The gate stacks described above may actually be permanent gate stacks as initially formed. Also, the processes described herein may be used to fabricate one or a plurality of semiconductor devices. The semiconductor devices may be transistors or like devices. For example, in an embodiment, the semiconductor devices are a metal-oxide semiconductor (MOS) transistors for logic or memory, or are bipolar transistors. Also, in an embodiment, the semiconductor devices have a three-dimensional architecture, such as a trigate device, an independently accessed double gate device, or a FIN-FET. One or more embodiments may be particularly useful for fabricating semiconductor devices at a 10 nanometer (10 nm) or smaller technology node.

Embodiments disclosed herein may be used to manufacture a wide variety of different types of integrated circuits and/or microelectronic devices. Examples of such integrated circuits include, but are not limited to, processors, chipset components, graphics processors, digital signal processors, micro-controllers, and the like. In other embodiments, semiconductor memory may be manufactured. Moreover, the integrated circuits or other microelectronic devices may be used in a wide variety of electronic devices known in the arts. For example, in computer systems (e.g., desktop, laptop, server), cellular phones, personal electronics, etc. The integrated circuits may be coupled with a bus and other components in the systems. For example, a processor may be coupled by one or more buses to a memory, a chipset, etc. Each of the processor, the memory, and the chipset, may potentially be manufactured using the approaches disclosed herein.

Figure 8:
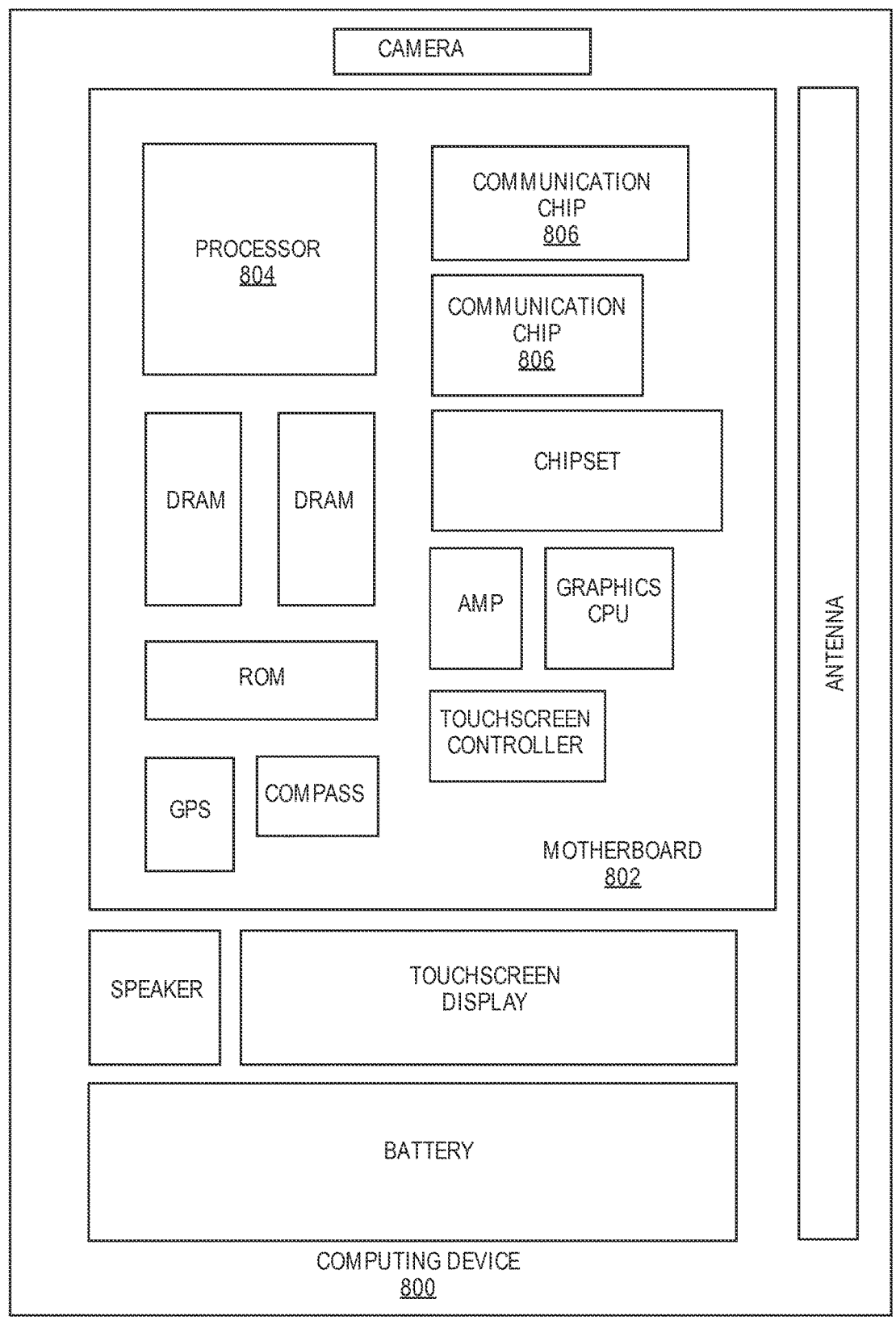
FIG. 8 illustrates a computing device in accordance with one implementation of the invention.

FIG. 8 illustrates a computing device 800 in accordance with one implementation of the invention. The computing device 800 houses a board 802. The board 802 may include a number of components, including but not limited to a processor 804 and at least one communication chip 806. The processor 804 is physically and electrically coupled to the board 802. In some implementations the at least one communication chip 806 is also physically and electrically coupled to the board 802. In further implementations, the communication chip 806 is part of the processor 804.

Depending on its applications, computing device 800 may include other components that may or may not be physically and electrically coupled to the board 802. These other components include, but are not limited to, volatile memory (e.g., DRAM), non-volatile memory (e.g., ROM), flash memory, a graphics processor, a digital signal processor, a crypto processor, a chipset, an antenna, a display, a touchscreen display, a touchscreen controller, a battery, an audio codec, a video codec, a power amplifier, a global positioning system (GPS) device, a compass, an accelerometer, a gyroscope, a speaker, a camera, and a mass storage device (such as hard disk drive, compact disk (CD), digital versatile disk (DVD), and so forth).

The communication chip 806 enables wireless communications for the transfer of data to and from the computing device 800. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. The communication chip 806 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. The computing device 800 may include a plurality of communication chips 806. For instance, a first communication chip 806 may be dedicated to shorter range wireless communications such as Wi-Fi and Bluetooth and a second communication chip 806 may be dedicated to longer range wireless communications such as GPS, EDGE, GPRS, CDMA, WiMAX, LTE, Ev-DO, and others.

The processor 804 of the computing device 800 includes an integrated circuit die packaged within the processor 804. In some implementations of embodiments of the invention, the integrated circuit die of the processor includes one or more structures, such as metallization structures formed at least in part by using inherently selective precursors for deposition of second or third row transition metal (e.g., tungsten or ruthenium) thin films, or MOS transistors including a metal gate layer formed at least in part by using inherently selective precursors for deposition of second or third row transition metal (e.g., tungsten or ruthenium) thin films, built in accordance with implementations of embodiments of the invention. The term "processor" may refer to any device or portion of a device that processes electronic data from registers and/or memory to transform that electronic data into other electronic data that may be stored in registers and/or memory.

The communication chip 806 also includes an integrated circuit die packaged within the communication chip 806. In accordance with another implementation of embodiments of the invention, the integrated circuit die of the communication chip includes one or more structures, such as metallization structures formed at least in part by using inherently selective precursors for deposition of second or third row transition metal (e.g., tungsten or ruthenium) thin films, or MOS transistors including a metal gate layer formed at least in part by using inherently selective precursors for deposition of second or third row transition metal (e.g., tungsten or ruthenium) thin films, built in accordance with implementations of embodiments of the invention.

In further implementations, another component housed within the computing device 800 may contain an integrated circuit die that includes one or more structures, such as metallization structures formed at least in part by using inherently selective precursors for deposition of second or third row transition metal (e.g., tungsten or ruthenium) thin films, or MOS transistors including a metal gate layer formed at least in part by using inherently selective precursors for deposition of second or third row transition metal (e.g., tungsten or ruthenium) thin films, built in accordance with implementations of embodiments of the invention.

In various implementations, the computing device 800 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In further implementations, the computing device 800 may be any other electronic device that processes data.

Figure 9:
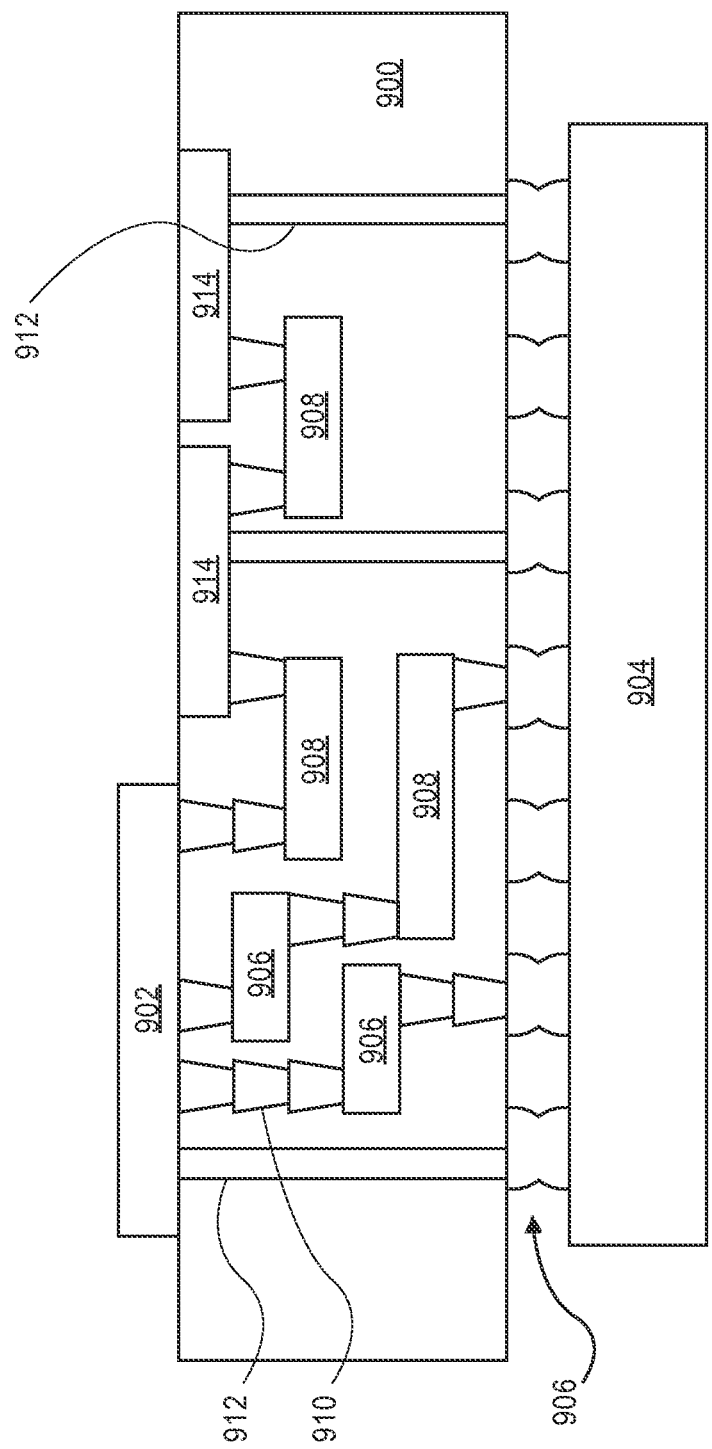
FIG. 9 is an interposer implementing one or more embodiments of the invention.

FIG. 9 illustrates an interposer 900 that includes one or more embodiments of the invention. The interposer 900 is an intervening substrate used to bridge a first substrate 902 to a second substrate 904. The first substrate 902 may be, for instance, an integrated circuit die. The second substrate 904 may be, for instance, a memory module, a computer motherboard, or another integrated circuit die. Generally, the purpose of an interposer 900 is to spread a connection to a wider pitch or to reroute a connection to a different connection. For example, an interposer 900 may couple an integrated circuit die to a ball grid array (BGA) 906 that can subsequently be coupled to the second substrate 904. In some embodiments, the first and second substrates 902/904 are attached to opposing sides of the interposer 900. In other embodiments, the first and second substrates 902/904 are attached to the same side of the interposer 900. And in further embodiments, three or more substrates are interconnected by way of the interposer 900.

The interposer 900 may be formed of an epoxy resin, a fiberglass-reinforced epoxy resin, a ceramic material, or a polymer material such as polyimide. In further implementations, the interposer may be formed of alternate rigid or flexible materials that may include the same materials described above for use in a semiconductor substrate, such as silicon, germanium, and other group III-V and group IV materials.

The interposer may include metal interconnects 908 and vias 910, including but not limited to through-silicon vias (TSVs) 912. The interposer 900 may further include embedded devices 914, including both passive and active devices. Such devices include, but are not limited to, capacitors, decoupling capacitors, resistors, inductors, fuses, diodes, transformers, sensors, and electrostatic discharge (ESD) devices. More complex devices such as radio-frequency (RF) devices, power amplifiers, power management devices, antennas, arrays, sensors, and MEMS devices may also be formed on the interposer 900. In accordance with embodiments of the invention, apparatuses or processes disclosed herein may be used in the fabrication of interposer 900.

Thus, embodiments of the present invention include inherently selective precursors for deposition of second or third row transition metal (e.g., tungsten or ruthenium) thin films.

In an embodiment, a ligand framework for second or third row transition metal complex formation includes a lithium complex of the formula:

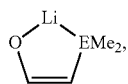

or a lithium complex of the formula:

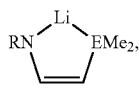

wherein E is nitrogen (N) or phosphorous (P), and R is an organic group.

In one embodiment, R is selected from the group consisting of methyl (Me), ethyl (Et), iso-propyl ($^i$Pr), tert-butyl ($^t$Bu), sec-butyl (sec-Bu), and dimethyl amino (Me$_2$N).

In an embodiment, a second or third row transition metal complex includes a metal complex of the formula:

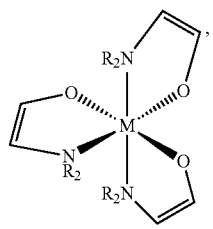

or an isomer thereof, or a metal complex of the formula:

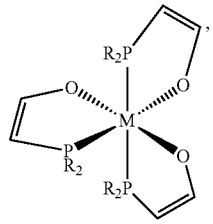

or an isomer thereof, or a metal complex of the formula:

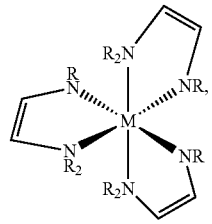

or an isomer thereof, or a metal complex of the formula:

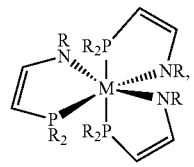

or an isomer thereof, wherein R$_2$ is dimethyl (Me$_2$) or diethyl (Et$_2$), and R is an organic group.

In one embodiment, R is selected from the group consisting of methyl (Me), ethyl (Et), iso-propyl ($^i$Pr), tert-butyl ($^t$Bu), sec-butyl (sec-Bu), and dimethyl amino (Me$_2$N).

In one embodiment, M is selected from the group consisting of tungsten (W) and ruthenium (Ru).

In an embodiment, a method of fabricating a thin metal film includes introducing precursor molecules proximate to a metal surface on or above a substrate. Each of the precursor molecules includes a second or third row transition metal center complexed with three heteroleptic bidentate ligands. The method also includes depositing a second or third row transition metal layer on the metal surface by thermally dissociating the ligands from the precursor molecules.

In one embodiment, thermally dissociating the ligands from the precursor molecules involves heating to a temperature approximately in the range of 50-600 degrees Celsius.

In one embodiment, depositing the second or third row transition metal layer on the metal surface involves depositing selectively on the metal surface without depositing on an adjacent dielectric surface.

In one embodiment, depositing the second or third row transition metal layer on the metal surface involves forming the second or third row transition metal layer to a thickness approximately equal to or less than 10 nanometers.

In one embodiment, depositing the second or third row transition metal layer comprises using an atomic layer deposition (ALD) or a chemical vapor deposition (CVD) process.

In one embodiment, depositing the second or third row transition metal layer involves depositing a tungsten layer.

In one embodiment, depositing the second or third row transition metal layer involves depositing a ruthenium layer.

What is claimed is:

1. A ligand framework for second or third row transition metal complex formation, the ligand framework comprising:

a lithium complex of the formula:

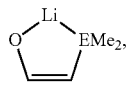

or a lithium complex of the formula:

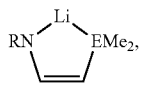

wherein E is nitrogen (N) or phosphorous (P), and R is an organic group.

2. The ligand framework of claim 1, wherein R is selected from the group consisting of methyl (Me), ethyl (Et), iso-propyl ($^i$Pr), tert-butyl ($^t$Bu), sec-butyl (sec-Bu), and dimethyl amino (Me$_2$N).

3. A second or third row transition metal complex, comprising:

a metal complex of the formula:

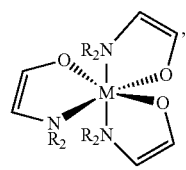

or an isomer thereof,
or a metal complex of the formula:

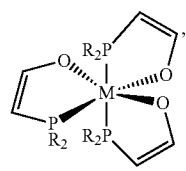

or an isomer thereof,
or a metal complex of the formula:

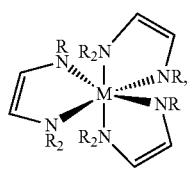

or an isomer thereof,
or a metal complex of the formula:

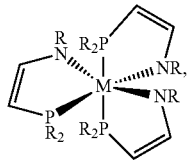

or an isomer thereof,
wherein R$_2$ is dimethyl (Me$_2$) or diethyl (Et$_2$), and R is an organic group.

4. The second or third row transition metal complex of claim 3, wherein R is selected from the group consisting of methyl (Me), ethyl (Et), iso-propyl ($^i$Pr), tert-butyl ($^t$Bu), sec-butyl (sec-Bu), and dimethyl amino (Me$_2$N).

5. The second or third row transition metal complex of claim 4, wherein M is selected from the group consisting of tungsten (W) and ruthenium (Ru).

6. A method of fabricating a thin metal film, the method comprising:

introducing precursor molecules proximate to a metal surface on or above a substrate, each of the precursor molecules comprising a second or third row transition metal center complexed with three heteroleptic bidentate ligands; and depositing a second or third row transition metal layer on the metal surface by thermally dissociating the ligands from the precursor molecules, wherein introducing the precursor molecules comprises introducing precursor molecules of the formula:

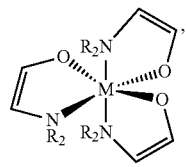

or an isomer thereof, wherein R$_2$ is dimethyl (Me$_2$) or diethyl (Et$_2$), and R is an organic group.

7. The method of claim 6, wherein thermally dissociating the ligands from the precursor molecules comprises heating to a temperature approximately in the range of 50-600 degrees Celsius.

8. The method of claim 6, wherein depositing the second or third row transition metal layer on the metal surface comprises depositing selectively on the metal surface without depositing on an adjacent dielectric surface.

9. The method of claim 6, wherein depositing the second or third row transition metal layer on the metal surface comprises forming the second or third row transition metal layer to a thickness approximately equal to or less than 10 nanometers.

10. The method of claim 6, wherein depositing the second or third row transition metal layer comprises using an atomic layer deposition (ALD) or a chemical vapor deposition (CVD) process.

11. The method of claim 6, wherein depositing the second or third row transition metal layer involves depositing a tungsten layer.

12. The method of claim 6, wherein depositing the second or third row transition metal layer involves depositing a ruthenium layer.

13. The method of claim 6, wherein the precursor molecules are formed from a lithium complex of the formula:

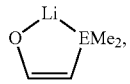

wherein E is nitrogen (N).

14. A method of fabricating a thin metal film, the method comprising:
introducing precursor molecules proximate to a metal surface on or above a substrate, each of the precursor molecules comprising a second or third row transition metal center complexed with three heteroleptic bidentate ligands; and
depositing a second or third row transition metal layer on the metal surface by thermally dissociating the ligands from the precursor molecules, wherein introducing the precursor molecules comprises introducing precursor molecules of the formula:

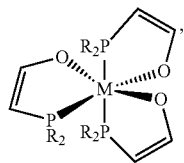

or an isomer thereof, wherein $R_2$ is dimethyl ($Me_2$) or diethyl ($Et_2$), and R is an organic group.

15. The method of claim 14, wherein the precursor molecules are formed from a lithium complex of the formula:

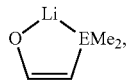

wherein E is phosphorous (P).

16. A method of fabricating a thin metal film, the method comprising:
introducing precursor molecules proximate to a metal surface on or above a substrate, each of the precursor molecules comprising a second or third row transition metal center complexed with three heteroleptic bidentate ligands; and
depositing a second or third row transition metal layer on the metal surface by thermally dissociating the ligands from the precursor molecules, wherein introducing the precursor molecules comprises introducing precursor molecules of the formula:

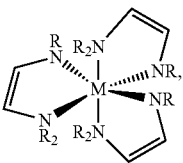

or an isomer thereof, wherein $R_2$ is dimethyl ($Me_2$) or diethyl ($Et_2$), and R is an organic group.

17. The method of claim 16, wherein the precursor molecules are formed from a lithium complex of the formula:

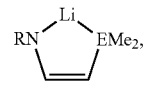

wherein E is nitrogen (N), and R is an organic group.

18. A method of fabricating a thin metal film, the method comprising:
introducing precursor molecules proximate to a metal surface on or above a substrate, each of the precursor molecules comprising a second or third row transition metal center complexed with three heteroleptic bidentate ligands; and
depositing a second or third row transition metal layer on the metal surface by thermally dissociating the ligands from the precursor molecules, wherein introducing the precursor molecules comprises introducing precursor molecules of the formula:

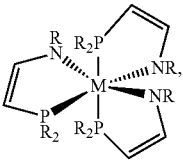

or an isomer thereof, wherein $R_2$ is dimethyl ($Me_2$) or diethyl ($Et_2$), and R is an organic group.

19. The method of claim 18, wherein the precursor molecules are formed from a lithium complex of the formula:

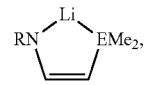

wherein E is phosphorous (P), and R is an organic group.

* * * * *